United States Patent
Levin et al.

(10) Patent No.: US 10,376,308 B2
(45) Date of Patent: Aug. 13, 2019

(54) DEVICES AND METHODS FOR TREATMENT OF HEART FAILURE BY SPLANCHNIC NERVE ABLATION

(71) Applicant: Axon Therapies, Inc., New York, NY (US)

(72) Inventors: Howard Levin, Teaneck, NJ (US); Mark Gelfand, New York, NY (US)

(73) Assignee: Axon Therapies, Inc., New York, NY (US)

( * ) Notice: Subject to any disclaimer, the term of this patent is extended or adjusted under 35 U.S.C. 154(b) by 433 days.

(21) Appl. No.: 15/017,351

(22) Filed: Feb. 5, 2016

(65) Prior Publication Data
US 2018/0110561 A1    Apr. 26, 2018

Related U.S. Application Data

(60) Provisional application No. 62/112,395, filed on Feb. 5, 2015, provisional application No. 62/162,266, filed on May 15, 2015.

(51) Int. Cl.
*A61B 18/14* (2006.01)
*A61N 1/00* (2006.01)
(Continued)

(52) U.S. Cl.
CPC ............ *A61B 18/1492* (2013.01); *A61N 1/00* (2013.01); *A61N 1/36017* (2013.01);
(Continued)

(58) Field of Classification Search
CPC ........ A61B 18/1492; A61B 2018/0022; A61B 2018/00267; A61B 2018/00404;
(Continued)

(56) References Cited

U.S. PATENT DOCUMENTS 3,301,258 A    1/1967   Werner
5,447,529 A    9/1995   Marchlinski et al.
(Continued)

FOREIGN PATENT DOCUMENTS

EP    2020943 B1    7/2015
EP    2755588 B1    5/2016
(Continued)

OTHER PUBLICATIONS

Adamopoulos et al; Comparison of different methods for assessing sympathovagal balance in chronic congestive heart failure secondary to coronary artery disease; The American Journal of Cardiology; 70(20); pp. 1576-1582; Dec. 15, 1992.
(Continued)

*Primary Examiner* — Jaymi E Della
*Assistant Examiner* — Sean W Collins
(74) *Attorney, Agent, or Firm* — Shay Glenn LLP

(57) ABSTRACT

A method for treating a heart failure patient by ablating a nerve of the splanchnic sympathetic nervous system to increase venous capacitance and reduce pulmonary blood pressure. A method including: inserting a catheter into a vein adjacent the nerve, applying stimulation energy and observing hemodynamic effects, applying ablation energy and observing hemodynamic effects, applying simulation energy after the ablation and observing hemodynamic effects.

33 Claims, 21 Drawing Sheets

(51) Int. Cl.
*A61N 1/36* (2006.01)
*A61B 18/00* (2006.01)
*A61B 90/00* (2016.01)

(52) U.S. Cl.
CPC .............. *A61B 2018/00214* (2013.01); *A61B 2018/00404* (2013.01); *A61B 2018/00434* (2013.01); *A61B 2018/00791* (2013.01); *A61B 2018/00863* (2013.01); *A61B 2018/00875* (2013.01); *A61B 2090/064* (2016.02)

(58) Field of Classification Search
CPC .......... A61B 2018/00434; A61B 2018/00577; A61B 2018/00702; A61B 2018/00732; A61B 2018/00791; A61B 2018/00863; A61B 2018/00875; A61B 2018/1407; A61B 2090/064; A61B 2018/00214; A61N 1/36017; A61N 1/00
See application file for complete search history.

(56) References Cited

U.S. PATENT DOCUMENTS

| | | | |
|---|---|---|---|
| 5,454,840 A | 10/1995 | Krakovsky et al. | |
| 5,458,626 A | 10/1995 | Krause | |
| 5,569,198 A | 10/1996 | Racchini | |
| 5,704,908 A | 1/1998 | Hofmann et al. | |
| 5,722,403 A | 3/1998 | McGee et al. | |
| 5,740,808 A | 4/1998 | Panescu et al. | |
| 5,797,903 A | 8/1998 | Swanson et al. | |
| 5,830,213 A | 11/1998 | Panescu et al. | |
| 5,836,874 A | 11/1998 | Swanson et al. | |
| 5,840,076 A | 11/1998 | Swanson et al. | |
| 5,846,239 A | 12/1998 | Swanson et al. | |
| 5,860,974 A | 1/1999 | Abele | |
| 5,868,736 A | 2/1999 | Swanson et al. | |
| 5,871,483 A | 2/1999 | Jackson et al. | |
| 5,891,136 A | 4/1999 | McGee et al. | |
| 5,925,038 A | 7/1999 | Panescu et al. | |
| 5,961,513 A | 10/1999 | Swanson et al. | |
| 6,044,846 A | 4/2000 | Edwards | |
| 6,058,331 A | 5/2000 | King | |
| 6,071,278 A | 6/2000 | Panescu et al. | |
| 6,099,526 A | 8/2000 | Whayne et al. | |
| 6,123,718 A | 9/2000 | Tu et al. | |
| 6,165,172 A | 12/2000 | Farley et al. | |
| 6,236,886 B1 | 5/2001 | Cherepenin et al. | |
| 6,395,325 B1 | 5/2002 | Hedge et al. | |
| 6,409,722 B1 | 6/2002 | Hoey et al. | |
| 6,425,877 B1 | 7/2002 | Edwards | |
| 6,454,766 B1 | 9/2002 | Swanson et al. | |
| 6,475,213 B1 | 11/2002 | Whayne et al. | |
| 6,569,160 B1 | 5/2003 | Goldin et al. | |
| 6,656,174 B1 | 12/2003 | Hegde et al. | |
| 6,658,279 B2 | 12/2003 | Swanson et al. | |
| 6,658,929 B2 | 12/2003 | Atkinson | |
| 6,668,198 B2 | 12/2003 | Swanson et al. | |
| 6,743,197 B1 | 6/2004 | Edwards | |
| 6,760,616 B2 | 7/2004 | Hoey et al. | |
| 6,832,114 B1 | 12/2004 | Whitehurst et al. | |
| 6,849,073 B2 | 2/2005 | Hoey et al. | |
| 6,885,888 B2 | 4/2005 | Rezai | |
| 6,890,315 B1 | 5/2005 | Levin et al. | |
| 6,954,977 B2 | 10/2005 | Maguire et al. | |
| 6,984,232 B2 | 1/2006 | Vanney et al. | |
| 7,054,689 B1 | 5/2006 | Whitehurst et al. | |
| 7,104,989 B2 | 9/2006 | Skarda | |
| 7,149,574 B2 | 12/2006 | Yun et al. | |
| 7,153,301 B2 | 12/2006 | Swartz et al. | |
| 7,236,822 B2 | 6/2007 | Dobak, III | |
| 7,239,912 B2 | 7/2007 | Dobak, III | |
| 7,282,050 B2 | 10/2007 | Starkebaum et al. | |
| 7,282,051 B2 | 10/2007 | Rioux et al. | |
| 7,285,199 B2 | 10/2007 | Mitsuhashi et al. | |
| 7,326,208 B2 | 2/2008 | Vanney et al. | |
| 7,330,762 B2 | 2/2008 | Boveja et al. | |
| 7,335,377 B2 | 2/2008 | Stern et al. | |
| 7,367,972 B2 | 5/2008 | Francischelli et al. | |
| 7,418,292 B2 | 8/2008 | Shafer | |
| 7,427,280 B2 | 9/2008 | Gerber | |
| 7,449,018 B2 | 11/2008 | Kramer | |
| 7,529,582 B1 | 5/2009 | DiLorenzo | |
| 7,532,938 B2 | 5/2009 | Machado et al. | |
| 7,551,964 B2 | 6/2009 | Dobak, III | |
| 7,599,736 B2 | 10/2009 | DiLorenzo | |
| 7,623,924 B2 | 11/2009 | Narciso, Jr. | |
| 7,689,276 B2 | 3/2010 | Dobak | |
| 7,689,277 B2 | 3/2010 | Dobak, III | |
| 7,702,386 B2 | 4/2010 | Dobak et al. | |
| 7,736,362 B2 | 6/2010 | Eberl et al. | |
| 7,769,442 B2 | 8/2010 | Shafer | |
| 7,778,703 B2 | 8/2010 | Gross et al. | |
| 7,860,570 B2 | 12/2010 | Whitehurst et al. | |
| 7,865,237 B2 | 1/2011 | Machado et al. | |
| 7,877,146 B2 | 1/2011 | Rezai et al. | |
| 7,921,657 B2 | 4/2011 | Littrup et al. | |
| 7,937,145 B2 | 5/2011 | Dobak | |
| 8,007,496 B2 | 8/2011 | Rioux et al. | |
| 8,155,744 B2 | 4/2012 | Rezai | |
| 8,229,564 B2* | 7/2012 | Rezai | A61F 2/82 607/42 |
| 8,241,273 B2 | 8/2012 | Whayne et al. | |
| 8,270,568 B2 | 9/2012 | Pitt | |
| 8,295,926 B2 | 10/2012 | Dobak, III | |
| 8,321,030 B2 | 11/2012 | Maniak et al. | |
| 8,399,443 B2 | 3/2013 | Seward | |
| 8,401,667 B2 | 3/2013 | Gustus et al. | |
| 8,414,508 B2 | 4/2013 | Thapliyal et al. | |
| 8,433,412 B1* | 4/2013 | Westlund | A61N 1/3962 607/122 |
| 8,483,835 B2 | 7/2013 | Errico et al. | |
| 8,611,496 B2 | 12/2013 | Terunuma et al. | |
| 8,676,326 B1 | 3/2014 | Farazi | |
| 8,676,362 B2 | 3/2014 | Gabel et al. | |
| 8,798,738 B2 | 8/2014 | Machado et al. | |
| 8,814,793 B2 | 8/2014 | Brabrand | |
| 8,911,439 B2 | 12/2014 | Mayse et al. | |
| 8,994,536 B2 | 3/2015 | Margon | |
| 8,998,894 B2 | 4/2015 | Mauch et al. | |
| 9,005,100 B2 | 4/2015 | Gnanashanmugam et al. | |
| 9,022,948 B2 | 5/2015 | Wang | |
| 9,028,472 B2 | 5/2015 | Mathur et al. | |
| 9,033,969 B2 | 5/2015 | Azamian et al. | |
| 9,037,259 B2 | 5/2015 | Mathur | |
| 9,072,902 B2 | 7/2015 | Mathur et al. | |
| 9,125,661 B2 | 9/2015 | Deem | |
| 9,125,668 B2 | 9/2015 | Subramaniam et al. | |
| 9,162,075 B2 | 10/2015 | Sluijter et al. | |
| 9,174,050 B2 | 11/2015 | Mathur et al. | |
| 9,199,091 B2 | 12/2015 | Danek et al. | |
| 9,245,182 B2 | 1/2016 | Jania et al. | |
| 9,278,196 B2 | 3/2016 | Fischell et al. | |
| 9,345,530 B2 | 5/2016 | Ballakur et al. | |
| 9,345,900 B2 | 5/2016 | Wu et al. | |
| 9,370,657 B2 | 6/2016 | Tehrani et al. | |
| 9,439,580 B2 | 9/2016 | Hatlestad et al. | |
| 9,439,598 B2 | 9/2016 | Shimada et al. | |
| 9,592,386 B2 | 3/2017 | Mathur et al. | |
| 9,603,659 B2 | 3/2017 | Subramaniam et al. | |
| 9,743,845 B2 | 8/2017 | Wang | |
| 9,757,193 B2 | 9/2017 | Zarins et al. | |
| 9,895,539 B1 | 2/2018 | Heit et al. | |
| 2003/0216792 A1 | 11/2003 | Levin et al. | |
| 2004/0247849 A1 | 12/2004 | Truckai | |
| 2005/0010095 A1 | 1/2005 | Stewart et al. | |
| 2005/0203462 A1 | 9/2005 | Katoh et al. | |
| 2005/0245923 A1 | 11/2005 | Christopherson et al. | |
| 2007/0167984 A1 | 7/2007 | Kieval et al. | |
| 2007/0213704 A1 | 9/2007 | Truckai et al. | |
| 2007/0224253 A1 | 9/2007 | Franklin | |
| 2009/0036794 A1 | 2/2009 | Stubhaug et al. | |
| 2009/0280178 A1 | 11/2009 | Hedge et al. | |
| 2010/0106207 A1* | 4/2010 | Dobak, III | A61K 31/135 607/3 |

(56) References Cited

U.S. PATENT DOCUMENTS

| | | | |
|---|---|---|---|
| 2010/0152731 A1 | 6/2010 | de la Rama et al. |
| 2010/0168820 A1 | 7/2010 | Maniak et al. |
| 2010/0241113 A1 | 9/2010 | Ingle |
| 2010/0249702 A1 | 9/2010 | Magana et al. |
| 2010/0305664 A1 | 12/2010 | Wingeier et al. |
| 2011/0022127 A1 | 1/2011 | Averina et al. |
| 2011/0028962 A1 | 2/2011 | Werneth et al. |
| 2011/0098761 A1 | 4/2011 | Wittenberger et al. |
| 2011/0224750 A1 | 9/2011 | Scheiner |
| 2011/0238083 A1 | 9/2011 | Moll et al. |
| 2012/0065554 A1 | 3/2012 | Pikus |
| 2012/0089047 A1 | 4/2012 | Ryba et al. |
| 2012/0143293 A1 | 6/2012 | Mauch et al. |
| 2012/0265198 A1 | 10/2012 | Crow et al. |
| 2012/0296329 A1 | 11/2012 | Ng |
| 2013/0035682 A1 | 2/2013 | Weil |
| 2013/0103026 A1* | 4/2013 | Kleshinski ............ A61B 18/082 606/41 |
| 2013/0226201 A1 | 8/2013 | Miller et al. |
| 2013/0237948 A1 | 9/2013 | Donders et al. |
| 2013/0282000 A1* | 10/2013 | Parsonage ............ A61B 18/18 606/33 |
| 2013/0296646 A1 | 11/2013 | Barbut et al. |
| 2013/0331813 A1 | 12/2013 | Barbut et al. |
| 2014/0031727 A1 | 1/2014 | Warnking |
| 2014/0058294 A1 | 2/2014 | Gross et al. |
| 2014/0058376 A1 | 2/2014 | Horn et al. |
| 2014/0058377 A1 | 2/2014 | Deem et al. |
| 2014/0067003 A1 | 3/2014 | Vase et al. |
| 2014/0088585 A1 | 3/2014 | Hill et al. |
| 2014/0088588 A1 | 3/2014 | Jarrard |
| 2014/0121641 A1 | 5/2014 | Fischell et al. |
| 2014/0214129 A1 | 7/2014 | Waataja et al. |
| 2014/0276718 A1 | 9/2014 | Turovskiy et al. |
| 2014/0276742 A1* | 9/2014 | Nabutovsky ........... A61B 18/18 606/33 |
| 2014/0303617 A1* | 10/2014 | Shimada ............ A61B 18/1492 606/41 |
| 2015/0080872 A1* | 3/2015 | Levin ................ A61M 5/14276 606/27 |
| 2015/0105659 A1 | 4/2015 | Salahieh et al. |
| 2015/0119674 A1 | 4/2015 | Fischell et al. |
| 2015/0141810 A1 | 5/2015 | Weadock |
| 2015/0141985 A1 | 5/2015 | Mayse et al. |
| 2015/0208949 A1 | 7/2015 | Tupin et al. |
| 2015/0245867 A1* | 9/2015 | Gross ................... A61B 5/0215 606/34 |
| 2015/0335286 A1 | 11/2015 | Boydell |
| 2016/0158554 A1 | 6/2016 | Graig |
| 2016/0163062 A1 | 6/2016 | Garber |
| 2016/0192981 A1 | 7/2016 | Dimmer et al. |
| 2016/0199127 A1 | 7/2016 | Prutchi |
| 2016/0220851 A1 | 8/2016 | Mayse et al. |
| 2016/0296171 A1 | 10/2016 | Drori et al. |
| 2016/0317621 A1 | 11/2016 | Bright |
| 2016/0374754 A1 | 12/2016 | Asirvatham et al. |
| 2017/0049989 A1 | 2/2017 | Kapural |
| 2017/0202614 A1 | 7/2017 | Gross et al. |
| 2017/0216602 A1 | 8/2017 | Waataja et al. |
| 2019/0069942 A1 | 3/2019 | Azamian et al. |

FOREIGN PATENT DOCUMENTS

| | | |
|---|---|---|
| EP | 2934357 B1 | 11/2017 |
| WO | WO2004/039428 A2 | 5/2004 |
| WO | WO2014/150887 A1 | 9/2014 |
| WO | WO2014/197625 A1 | 12/2014 |
| WO | WO2016/084081 A2 | 6/2016 |
| WO | WO2016/090175 A1 | 6/2016 |
| WO | WO2016/132340 A1 | 8/2016 |
| WO | WO2017/074920 A1 | 5/2017 |
| WO | WO2017/096007 A1 | 6/2017 |
| WO | WO2017/197625 A1 | 11/2017 |
| WO | WO2018/023132 A1 | 2/2018 |

OTHER PUBLICATIONS

Andren-Sandberg et al.; Thoracoscopic splanchnicectomy for chronic, severe pancreatic pain; In Seminars in Laparoscopic Surgery; 3(1); Sage CA: Thousand Oaks CA; Sage Publications; pp. 29-33; Mar. 1, 1996.

Barnes et al.; Haemodynamic responses to stimulation of the splanchnic and cardiac sympathetic nerves in the anaesthetized cat; The Journal of Physiology; 378; pp. 417-436; Sep. 1986.

Bauereisen et al.; The importance of mesenteric mechanoreceptors for the reflex innervation of resistance blood vessels capacity blood vessels in the splanchnic area; Pflugers Archiv fur die gesamte Physiologie des Menschen and der Tiere; 276; pp. 445-455; Jan. 1963.

Bradley et al.; Nerve blocks and neuroablative surgery for chronic pancreatitis; World J. Surg.; 27(11); pp. 1241-1248; Nov. 1, 2003.

Brunner et al.; Carotid sinus baroreceptor control of splanchnic resistance and capacity. Am J Physiol.; 255; pp. H1305-1310; Dec. 1988.

Buscher et al.; Limited effect of thoracoscopic splanchnicectomy in the treatment of severe chronic pancreatitis pain: a prospective long-term analysis of 75 cases; Surgery; 143(6); pp. 715-722; Jun. 30, 2008.

Carneiro et al.; Change in liver blood flow and blood content in dogs during direct and reflex alteration of hepatic sympathetic nerve activity; Circulation Research; 40(2); pp. 150-158; Feb. 1, 1977.

Cuschieri et al.; Bilateral endoscopic splanchnicectomy through a posterior thoracoscopic approach; Journal of the Royal College of Surgeons of Edinburgh; 39(1); pp. 44-47; Feb. 1994.

Diedrich et al.; Segmental orthostatic fluid shifts; Clinical autonomic research;14(3); pp. 146-147; Jun. 2004.

Edwards; The glycogenolytic response to stimulation of the splanchnic nerves in adrenalectomized calves, sheep, dogs, cats and pigs; J Physiol.; 213; pp. 741-759; Mar. 1971.

Eisenberg et al.; Neurolytic celiac plexus block for treatment of cancer pain: A meta-analysis; Anesth Analg; 80(2); pp. 290-295; Feb. 1995.

Ferrara et al; Hemodynamics of the splanchnic and systemic circulation after hypotonic water load-comparison between normal subjects and patients with congestive heart failure; Acta Cardiologica; 38(2); pp. 81-88; Dec. 1982.

Folkow et al.; The Effect of Graded Vasoconstrictor Fibre Stimulation on the Intestinal Resistance and Capacitance Vessels; Acta physiologica Scandinavica; 61; pp. 445-457; Aug. 1964.

Foss et al.; Reversal of genetic salt-sensitive hypertension by targeted sympathetic ablation; Hypertension; 61(4); pp. 806-811; Apr. 1, 2013.

Francis et al.; Clinical notes, suggestions and new instrument; JAMA; 134 (1); pp. 20-21; May 3, 1947.

Garcea et al.; Percutaneous splanchnic nerve radiofrequency ablation for chronic abdominal pain; ANZ Journal of Surgery; 75(8); pp. 640-644; Aug. 1, 2005.

Giraudo et al.; Endoscopic palliative treatment of advanced pancreatic cancer: Thoracoscopic splanchnicectomy and laparoscopic gastrojejunostomy; Annals of Oncology; 10(4); pp. S278-S280; Jan. 1, 1999.

Goldblatt et al.; Studies on experimental hypertension II: The effect of resection of splanchnic nerves on experimental renal hypertension; The Journal of Experimental Medicine; 65(2); pp. 233-241; Feb. 1, 1937.

Goroszeniuk et al.; Permanent percutaneous splanchnic nerve neuromodulation for management of pain due to chronic pancreatitis: A case report; Neuromodulation; ;14(3); pp. 253-257; May-Jun. 2011.

Greenway et al.; Role of splanchnic venous system in overall cardiovascular homeostasis; In Federal Proceedings; 42(6); pp. 1678-1684; Apr. 1983.

Greenway; Blockade of reflex venous capacitance responses in liver and spleen by hexamethonium, atropine, and surgical section; Canadian journal of physiology and pharmacology; 69(9); pp. 1284-1287; Sep. 1991.

(56) References Cited

OTHER PUBLICATIONS

Griffith et al.; The vasomotor control of the liver circulation; American Journal of Physiology; 95(1); pp. 20-34; Oct. 1930.
Griffith et al.; Vasomotor Control of the Liver Circulation. Proceedings of the Society for Experimental Biology and Medicine; 27(7); pp. 673-674; Apr. 1930.
Herman et al.; Splenic afferents and some of their reflex responses; American Journal of Physiology-Regulatory, Integrative and Comparative Physiology; 242(3); pp. R247-R254; Mar. 1982.
Ihse et al.; Bilateral thoracoscopic splanchnicectomy: effects on pancreatic pain and function; Annals of Surgery; 230(6); pp. 785-791; Dec. 1, 1999.
Ischia et al; A new approach to the neurolytic block of the coeliac plexus: the transaortic technique; Pain; 16(4); pp. 333-341; Aug. 31, 1983.
Johnson et al.; An open randomized comparison of clinical effectiveness of protocol-driven opioid analgesia, celiac plexus block or thoracoscopic splanchnicectomy for pain management in patients with pancreatic and other abdominal malignancies; Pancreatology; 9(6); pp. 755-763; Jan. 1, 2009.
Kang et al.; Bilateral thoracoscopic splanchnicectomy with sympathectomy for managing abdominal pain in cancer patients; Am J Surg; 194(1); pp. 23-29; Jul. 2007.
Katri et al.; Thoracoscopic splanchnicectomy for pain control in irresectable pancreatic cancer; Journal of Laparoendoscopic and Advanced Surgical Techniques; 18(2); pp. 199-203; Apr. 1, 2008.
Kaufman et al.; Effect of portal hypertension on splenic blood flow, intrasplenic extravasation and systemic blood pressure; American Journal of Physiology-Regulatory, Integrative and Comparative Physiology; 284 (6); pp. R1580-1585; Jun. 1, 2003.
King et al.; Splanchnic circulation is a critical neural target in angiotensin II salt hypertension in rats; Hypertension; 50(3); pp. 547-556; Sep. 2007.
Krishna et al.; Video-assisted thoracoscopic sympathectomy-splanchnicectomy for pancreatic cancer pain; Journal of Pain and Symptom Management; 22(1); pp. 610-616; Jul. 1, 2001.
Lang-Lazdunski et al.; Videothoracoscopic splanchnicectomy for intractable pain from adrenal metastasis; Ann Thorac Surg; 73(4); pp. 1290-1292; Apr. 2002.
Le Pimpec Barthes; Thoracoscopic splanchnicectomy for control of intractable pain in pancreatic cancer; The Annals of Thoracic Surgery; 65(3); pp. 810-813; Mar. 31, 1998.
Leksowski; Thoracoscopic splanchnicectomy for the relief of pain due to chronic pancreatitis; Surg Endosc.; 15(6); pp. 592-596; Jun. 2001.
Lica et al.; Thoracoscopic left splanchnicectomy—role in pain control in unresectable pancreatic cancer. Initial experience; Chirurgia; 109(3); pp. 313-317; May-Jun. 2014.
Lieberman et al.; Celiac plexus neurolysis with the modified transaortic approach; Radiology; 175(1); pp. 274-276; Apr. 1990.
Lillemoe et al; Chemical splanchnicectomy in patients with unresectable pancreatic cancer. A prospective randomized trial; Annals of Surgery; 217(5); pp. 447-457; May 1, 1993.
Lin et al.; Bilateral thoracoscopic lower sympathetic-splanchnicectomy for upper abdominal cancer pain. The European journal of surgery; Supplement 572; pp. 59-62; 1994.
Lonroth et al.; Unilateral left-side thoracoscopic sympathectomy for visceral pain control: a pilot study; The European Journal of Surgery; 163(2); pp. 97-100; Feb. 1, 1997.
Maass-Moreno et al.; Carotid baroreceptor control of liver and spleen volume in cats; Am J Physiol; 260(1 Pt 2); pp. H254-259; Jan. 1991.
Maher et al.; Thoracoscopic splanchnicectomy for chronic pancreatitis pain; Surgery; 120(4); pp. 603-610; Oct. 1996.
Myhre et al.; Monitoring of celiac plexus block in chronic pancreatitis; Pain; 38(3); pp. 269-274; Sep. 1989.
Nakazato et al; Extrinsic innervation of the canine abdominal vena cava and the origin of cholinergic vasoconstrictor nerves; J. Physiol.; 328; pp. 191-203; Jul. 1982.

Pan et al.; Differential responses of regional sympathetic activity and blood flow to visceral afferent stimulation; Am J Physiol Regul Integr Comp Physiol.; 280(6); pp. R1781-1789; Jun. 2001.
Pietrabissa et al.; Thoracoscopic splanchnicectomy for pain relief in unresectable pancreatic cancer; Archives of Surgery; 135(3); pp. 332-335; Mar. 1, 2000.
Plancarte et al.; Management of chronic upper abdominal pain in cancer: transdiscal blockage of the splanchnic nerves; Regional Anesthesia and Pain Medicine; 35(6); pp. 500-506; Nov. 1, 2010.
Prasad et al.; Thoracoscopic splanchinicectomy as a palliative procedure for pain relief in carcinoma pancreas; Journal of Minimal Access Surgery; 5(2); pp. 37-39; (Author Manuscript); Apr. 1, 2009.
Raj; Celiac plexus/splanchnic nerve blocks; Techniques in Regional Anesthesia and Pain Management; 5(3); pp. 102-115; Jul. 2001.
Raj et al.; Radiofrequency lesioning of splanchnic nerves; Pain Practice; 2(3); pp. 242-247; Sep. 2002.
Saenz et al.; Thoracoscopic splanchicectomy for pain control in patients with unresectable carcinoma of the pancreas; Surgical Endoscopy; 14(8); pp. 717-720; Aug. 1, 2000.
Sastre et al.; Transhiatal bilateral splanchnicotomy for pain control in pancreatic cancer: basic anatomy, surgical technique, and immediate results in fifty-one cases; Surgery; 111(6); pp. 640-646; Jun. 1992.
Scott-Douglas et al.; Effects of acute volume loading and hemorrhage on intestinal vascular capacitance: a mechanism whereby capacitance modulates cardiac output; Can. J. Cardiol.; 18(5); pp. 515-522; May 5, 2002.
Shimada et al.; Clinical evaluation of transhiatal bilateral splanchnicotomy for patients with intractable suprmesenteric pain; Surgery Today; 29(11); pp. 1136-1140; Nov. 1999.
Smigielski et al.; Assessment of quality of life in patients with non-operated pancreatic cancer after videothoracoscopic splanchnicectomy; Videosurgery and Other Miniinvasive Techniques; 6(3); pp. 132-137; Sep. 1, 2011.
Stefaniak et al.; A comparison of two invasive techniques in the management of intractable pain due to inoperable pancreatic cancer; European Journal of Surgical Oncology; 31(7); pp. 768-773; Sep. 30, 2005.
Yan et at.; Neurolytic celiac plexus block for pain control in unresectable pancreatic cancer; Am J Gastroenterol; 102(2); pp. 430-438; Feb. 2007.
Takahashi et al.; Thoracoscopic splanchnicectomy for the relief of intractable pain; Surgical Endoscopy; 10(1); pp. 65-68; Jan. 1, 1996.
Tavassoli et al.; Thoracoscopic splanchnicectomy for pain control in urresectable pancreatic cancer; Journal of Cardio-Thoracic Medicine; 1(2); pp. 53-56; Aug. 6, 2013.
Tsybenko et al.; Central nervous control of hepatic circulation; J Aut Nerv Sys; 33(3); pp. 255-266; May 1991.
Van Vliet et al.; Time course of renal responses to greater splanchnic nerve stimulation; American Journal of Physiology Regulatory, Integrative and Comparative Physiology; 260(5); pp. R894-R905; May 1991.
Verhaegh et al.; Percutaneous radiofrequency ablation of the splanchnic nerves with chronic pancreatitis: results of single and repeated procedures in 11 patients; Pain Practice; 13(8); pp. 621-626; (Author Manuscript); Nov. 1, 2013.
Wilkins et al.; The effect of splanchnic sympathectomy in hypertensive patients upon estimated hepatic blood flow in the upright as contrasted with the horizontal position; Journal of Clinical Investigation; 30(3); pp. 312-317; Mar. 1951.
Worsey et al.; Thoracoscopic pancreatic denervation for pain control in irrsectable pancreatic cancer; British Journal of Surgery; 80(8); pp. 1051-1052; Aug. 1, 1993.
Gelfand et al.; U.S. Appl. No. 15/293,021 entitled "Devices and methods for treatment of heart failure via electrical modulation of a splanchnic nerve," filed Oct. 13, 2016.
Brooksby et al.; Dynamic changes in splanchnic blood flow and blood volume in dogs during activation of sympathetic nerves; Circulation Research; XXIX(3); pp. 227-238; Sep. 1971.
Burkhoff et al.; Why does pulmonary venous pressure rise after on of LV dysfunction: a theoretical analysis; Am. J. Physiol.; 265(5, pt. 2); pp. H1819-1828; Nov. 1993.

(56) References Cited

OTHER PUBLICATIONS

Fujita; Splanchnic circulation following coeliac plexus block; Acta Anaesthesiol Scand.; 32(4); pp. 323-327; May 1988.

Greenway; Blockade of reflex venous capacitance responses in liver and spleen by hexamethonium, atropine, and surgical section; Can. J. Physiol. Pharmacol.; 69(9); 1284-1287; Sep. 1991.

Kimura et al.; Application of electrical impedance analysis for diagnosis of a pulmonary mass; Chest; 105(6); pp. 1679-1682; Jun. 1994.

Nath et al.; Biophysics and pathology of catheter energy delivery systems; Progress in Cardiovascular Diseases; XXXVII(4); pp. 185-204; Jan./Feb. 1995.

Wroclaw Medical Univ. (Poland); Removing a section of nerve visceral improved (press release; with machine translation); retrieved Oct. 10, 2016 from the internet: http://www.zdrowie.abc.com.pl/aktualnosci/wroclaw-usuniecie-fragmentu-nerwu-trzewnego-poprawilo-u-chorej-wydolnosc-serca,25247.html; 5 pgs.; Sep. 23, 2016.

Cody et al.; Captopril kinetics in chronic congestive heart failure; Clin pharmacol Ther.; 32(6); pp. 721-726; Dec. 1982.

Edwards Lifesciences; ClearSight System (brochure; No. AR11578); 4 pgs.; © 2014.

Fiaccadori et al.; Ultrafiltration in Heart Failure; Am Heart J.; 161(3); pp. 439-449; Mar. 2011.

Gambro®; Aquadex FlexFlowTM (brochure, No. L5189 Rev. B); 4 pgs.; © 2011 (August).

Fallick et al.; Sympathetically mediated changes in capacitance: Redistribution of the venous reservoir as a cause of decompensation; Circulation: Heart Failure; 4; pp. 669-675; Sep. 2011.

Levin et al.; U.S. Appl. No. 15/017,260 entitled "Devices And Methods For Treatment Of Heart Failure By Splanchnic Nerve Ablation," filed Feb. 5, 2016.

Levin et al., U.S. Appl. No. 16/318,447 entitled "Devices, systems, and methods for treatment of heart failure by splanchnic nerve ablation," filed Jan. 17, 2019.

Panescu et al.; U.S. Appl. No. 16/222,823 entitled "Methods and devices for endovascular ablation of a splanchnic nerve," filed Dec. 17, 2018.

\* cited by examiner

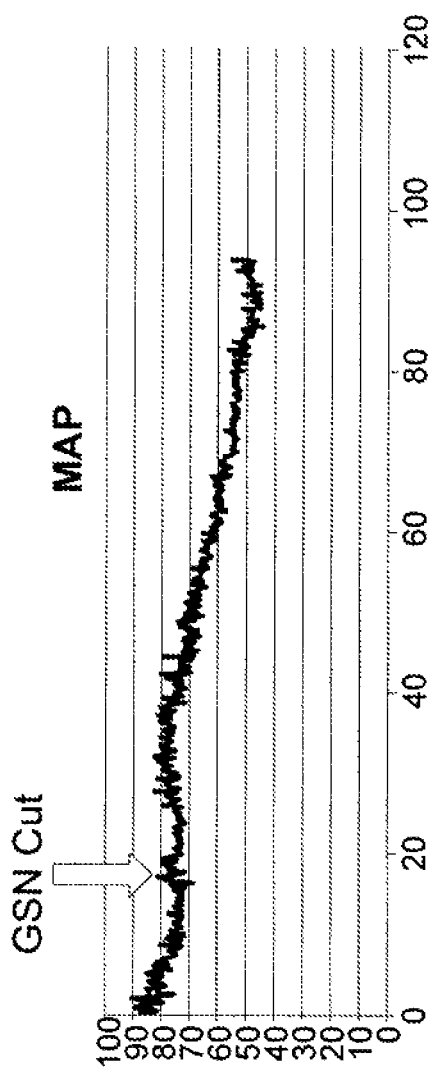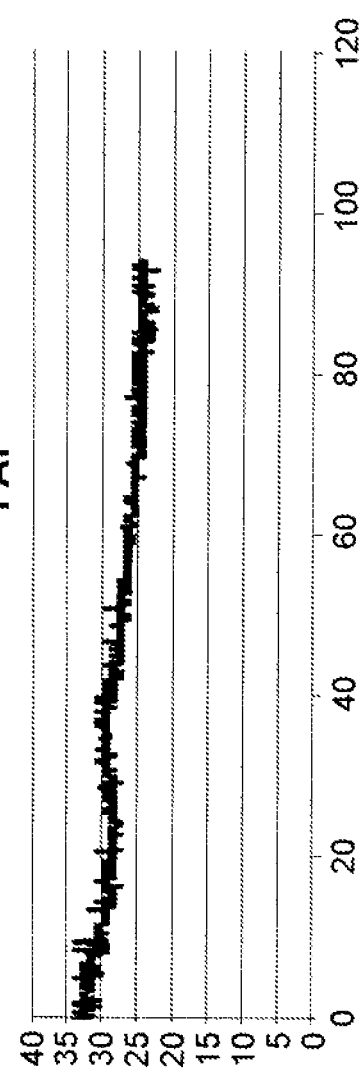

DEVICES AND METHODS FOR TREATMENT OF HEART FAILURE BY SPLANCHNIC NERVE ABLATION

RELATED APPLICATIONS

This application claims the benefit of U.S. Provisional Patent Applications 62/112,395 filed Feb. 5, 2015, and 62/162,266, filed May 15, 2015, the entirety of both these applications is incorporated by reference.

BACKGROUND

Heart failure (HF) is a medical condition that occurs when the heart is unable to pump sufficiently to sustain the organs of the body. Heart failure is a serious condition and affects millions of patients in the United States and around the world.

In the United States alone, about 5.1 million people suffer from heart failure and according to the Center for Disease Control, the condition costs the nation over $30 billion in care, treatments, medications, and lost production. The normal healthy heart is a muscular pump that is, on average, slightly larger than a fist. It pumps blood continuously through the circulatory system to supply the body with oxygenated blood. Under conditions of heart failure, the weakened heart cannot supply the body with enough blood and results in cardiomyopathy (heart muscle disease) characterized by fatigue and shortness of breath, making even everyday activities such as walking very difficult.

Oftentimes, in an attempt compensate for this dysfunction, the heart and body undergo physiological changes that temporarily mask the inability of the heart to sustain the body. These changes include the enlargement of heart chamber, increased cardiac musculature, increased heart rate, raised blood pressure, poor blood flow, and imbalance of body fluids in the limbs and lungs.

One common measure of heart health is left ventricular ejection fraction (LVEF) or ejection fraction. By definition, the volume of blood within a ventricle immediately before a contraction is known as the end-diastolic volume (EDV). Likewise, the volume of blood left in a ventricle at the end of contraction is end-systolic volume (ESV). The difference between EDV and ESV is stroke volume (SV). SV describes the volume of blood ejected from the right and left ventricles with each heartbeat. Ejection fraction (EF) is the fraction of the EDV that is ejected with each beat; that is, it is SV divided by EDV. Cardiac output (CO) is defined as the volume of blood pumped per minute by each ventricle of the heart. CO is equal to SV times the heart rate (HR).

Cardiomyopathy, in which the heart muscle becomes weakened, stretched, or exhibits other structural problems, can be further categorized into systolic and diastolic dysfunction based on ventricular ejection fraction.

Systolic dysfunction is characterized by a decrease in myocardial contractility. A reduction in the LVEF results when myocardial contractility is decreased throughout the left ventricle. CO is maintained in two ways: left ventricular enlargement results in a higher SV and an increase in contractility as a result of the increased mechanical advantage from stretching the heart. However, these compensatory mechanisms are eventually exceeded by continued weakening of the heart and CO decreases, resulting in the physiologic manifestations of HF. The left side of the heart cannot pump with enough force to push a sufficient amount of blood into the systemic circulation. This leads to fluid backing up into the lungs and pulmonary congestion. In general terms, systolic dysfunction is defined as an LVEF less than 40% and heart failure in these patients can be broadly categorized as heart failure with reduced ejection fraction (HFrEF).

Diastolic dysfunction refers to cardiac dysfunction in which left ventricular filling is abnormal and is accompanied by elevated filling pressures. In diastole, while the heart muscle is relaxed the filling of the left ventricle is a passive process that depends on the compliance (defined by volume changes over pressure changes), or distensibility, of the myocardium or heart muscle. When the ventricles are unable to relax and fill, the myocardium may strengthen in an effort to compensate to poor SV. This subsequent muscle hypertrophy leads to even further inadequate filling. Diastolic dysfunction may lead to edema or fluid accumulation, especially in the feet, ankles, and legs. Furthermore, some patients may also have pulmonary congestion as result of fluid buildup in the lungs. For patients with HF but without systolic dysfunction, diastolic dysfunction is the presumed cause. Diastolic dysfunction is characteristic of not only HCM, which is characterized by the thickening of heart muscle, but also RCM, which is characterized by rigid heart muscle that cannot stretch to accommodate passive filling. In general terms, diastolic dysfunction is defined as a LVEF of greater than 40% and HF in these patients can be broadly categorized as heart failure with preserved ejection fraction (HFpEF).

While a number of drug therapies successfully target systolic dysfunction and HFrEF, for the large group of patients with diastolic dysfunction and HFpEF no promising therapies have yet been identified. The clinical course for patients with both HFrEF and HFpEF is significant for recurrent presentations of acute decompensated heart failure (ADHF) with symptoms of dyspnea, decreased exercise capacity, peripheral edema etc. Recurrent admissions for ADHF utilize a large part of current health care resources and could continue to generate enormous costs.

While the pathophysiology of HF is becoming increasingly better understood, modern medicine has, thus far, failed to develop new therapies for chronic management of HF or recurrent ADHF episodes. Over the past few decades, strategies of ADHF management and prevention have and continue to focus on the classical paradigm that salt and fluid retention is the cause of intravascular fluid expansion and cardiac decompensation. Increasing evidence suggests that fluid homeostasis and control of intravascular fluid distribution is disrupted in patients with HF. Disregulation of this key cardiovascular regulatory component could not only explain findings in chronic HF but also in ADHF. Consequently, blocking of the autonomic nervous system to alter fluid distribution in the human body could be used as a therapeutic intervention.

Additionally, the classical understanding of HF pathophysiology emphasizes the mechanism of poor forward flow (i.e., low CO), resulting in neurohumoral, or sympathetic nervous system (SNS) up-regulation. However, new evidence emphasizes the concurrent role of backward failure (i.e., systemic congestion) in the pathophysiology and disease progression of HF. Coexisting renal dysfunction with diuretic resistance often complicates the treatment of HF and occurs more frequently in patients with increased cardiac filling pressures. Chronic congestive heart failure (CHF) is characterized by longstanding venous congestion and increased neurohumoral activation. Critically important has been the identification of the splanchnic vascular bed as a major contributor to blood pooling and cardiac physiology. Newly evolving methods and devices involving sympathetic nervous system blocking and manipulation of systems including the splanchnic vascular bed have opened novel avenues to approach the treatment of heart disease. In particular, the role of sympathetic nerves that innervate smooth muscle in the walls of splanchnic veins have become better known. In the case of hyperactivity of these nerves they became a novel target in the treatment of CHF.

SUMMARY OF THE INVENTION

In view of the foregoing, it would be desirable to provide an apparatus and methods to affect neurohumoral activation for the treatment of HF and particularly diastolic HF, (HFpEF).

The present invention may be used to provide an improved treatment option for patients suffering from HF by ablating the splanchnic nerves (e.g., greater, lesser and least) that innervate organs and vasculature of the abdominal compartment and the greater splanchnic nerve (GSN) in particular. By selectively ablating specific nerves, the invention provides a novel method and device that can affect circulating blood volume, pressure, blood flow and overall heart and circulatory system functions. In this way, the present invention helps to introduce novel solutions to treat HF and particularly HFpEF based on the most contemporary physiological theories regarding HF.

About 5% of the total body water is located within the vasculature in the form of blood. The venous system contains approximately 70% of total blood volume and is roughly 30 times more compliant than the arterial system. Venous compliance is a measure of the ability of a hollow organ or vessel to distend and increase in volume with increasing internal pressure. A number of mechanisms are involved in regulation of volume, most importantly the neurohormonal system. On the arterial side, flow and resistance are regulated by resistance vessels. The sympathetic nervous system plays a major role in determining systemic vascular resistance (SVR) predominantly through activation and deactivation of cardiopulmonary and arterial baroreflexes, as well as through changes in circulating norepinephrine.

Capacitance is a determinant of the venous vascular function and higher vascular capacitance means more blood can be stored in the respective vasculature. The autonomic nervous system is the main regulatory mechanism of vascular capacitance.

Circulating blood is distributed into two physiologically but not anatomically separate compartments: the "venous reservoir" and "effective circulatory volume". The term "venous reservoir" (or "unstressed volume") refers to the blood volume that resides mainly in the splanchnic vascular bed and does not contribute to the effective circulating volume. The venous reservoir that is also referred to as "unstressed volume" or "vascular capacitance" can be recruited through a number of mechanisms like activation of the sympathetic nervous system, drugs, or hormones.

The term "effective circulatory volume" (or "stressed volume") refers to blood that is present mainly in the arterial system and in non-splanchnic venous vessels and is one of the main determinants of preload of the heart. The stressed blood volume and systemic blood pressure are regulated by the autonomic nervous system of which the sympathetic nervous system is a part.

The unstressed volume of blood is mostly contained in the splanchnic reservoir or "splanchnic vascular bed". The splanchnic reservoir consists of vasculature of the visceral organs including the liver, spleen, small and large bowel, stomach, as well as the pancreas. Due to the low vascular resistance and high capacitance the splanchnic vascular bed receives about 25% of the CO and the splanchnic veins contain anywhere from 20% to 50% of the total blood volume.

Consequently, the splanchnic vascular bed serves as the major blood reservoir, which can take up or release, actively and passively, the major part of any change in circulating blood volume.

While experimenting with cadavers and animals inventors made two important discoveries: (a) venous reservoir can be artificially manipulated and modified by selectively ablating or stimulating the GSN, and (b) in humans and some animals the GSN, although hidden deep in the body, can be accessed very closely from superficial veins, through the venous system, and the azygos veins.

Splanchnic veins are considerably more compliant than veins of the extremities. Animal and human studies demonstrate that the splanchnic reservoir can not only store considerable amounts of blood, but blood can also be actively or passively recruited from it into the systemic circulation in response to variations of the venous return of blood to the heart and physiologic need for heart preload. One of the main determinants of active recruitment is sympathetic nerve activity (SNA), which through hormones and a neurotransmitters epinephrine and norepinephrine causes venoconstriction, thereby reducing splanchnic capacitance and increasing effective circulatory volume. This can be explained by a large numbers of adrenergic receptors in the splanchnic vasculature that are sensitive to changes to the sympathetic nervous system. Compared with arteries, splanchnic veins contain more than five (5) times the density of adrenergic terminals. The consequence is a more pronounced venous vasomotor response in the splanchnic system compared to other vascular regions.

The splanchnic vascular bed is well suited to accommodate and store large amounts of blood as well as shift blood back into active circulation, naturally acting in a temporary blood volume storage capacity. The high vascular capacitance allows the splanchnic vascular bed to maintain preload of the heart and consequently arterial blood pressure and CO over a wide range of total body volume changes. Once the storage capacity of the splanchnic vascular bed is reached, increases in total body fluid express themselves as increased cardiac preload beyond physiologic need and eventually extravascular edema and particularly fluid accumulation in the lungs that is a symptom common in HF.

Increased activation of the sympathetic nervous system (SNS) and the neurohormonal activation along with increases in body fluids and salts have long been debated as causes versus effects of HF. It has been previously suggested that in HF redistribution of the splanchnic reservoir, driven by increased SNA to the splanchnic vascular bed leading to decreased venous compliance and capacitance, is responsible for increased intra-cardiac filling pressure (preload) in the absence of increases in total body salt and water. HF is marked by chronic over-activity of the SNS and the neurohormonal axis. It is now suggested that SNA and neurohormonal activation result in an increased vascular tone and consequently in decreased vascular capacitance of the splanchnic vascular bed. While peripheral vascular capacitance is mostly unchanged in HFpEF and HFrEF compared to controls, the vascular capacitance of the splanchnic vascular can be significantly decreased.

So-called "acute HF" is initiated by a combination of two pathways: cardiac and vascular. The "cardiac pathway" is generally initiated by a low cardiac contractility reserve, while the "vascular pathway" is common to acute HF (AHF) that exhibits mild to moderate decrease in cardiac contractility reserve.

In ADHF, which is characterized by worsening of the symptoms: typically shortness of breath (dyspnea), edema, and fatigue, in a patient with existing heart disease, the cardiac filling pressures generally start to increase more than 5 days preceding an admission. While this could reflect a state of effective venous congestion following a build-up of volume, nearly 50% of patients gain only an insignificant amount of weight (<1 kg) during the week before admission. This means that in about 50% of cases, decompensated HF is not caused by externally added fluid, but rather symptoms and signs of congestion can be entirely explained by redistribution of the existing intravascular volume.

Acute increases in sympathetic nervous tone due to a variety of known triggers like cardiac ischemia, arrhythmias, inflammatory activity and psychogenic stress and other unknown triggers can disrupt the body's balance and lead to a fluid shift from the splanchnic venous reservoir into the effective circulation. This results ultimately in an increase in preload and venous congestion. This explains the finding that in ADHF in both HFrEF and HFpEF was preceded by a significant increase in diastolic blood pressures.

In many patients with HFpEF relatively small increases in diastolic pressures/preload can result in decompensation due to impaired relaxation of the ventricles. Thus patients with HFpEF are more sensitive to intrinsic or extrinsic fluid shifts.

Chronic CHF is characterized by longstanding venous congestion and increased neurohumoral activation. Like in acute heart failure, the splanchnic vascular bed has been identified as a major contributor to HF pathophysiology. Chronic decrease in vascular compliance and capacitance makes the human body more susceptible to recurrent acute decompensations, making significant the consequences of chronic congestion of the splanchnic compartment. While the splanchnic vascular compartment is well suited to accommodate acute fluid shifts (e.g. change of posture to orthostasis, exercise and dietary intake of water), the regulation of the splanchnic vascular bed becomes maladaptive in chronic disease states associated with increased total body volume and increased splanchnic vascular pressure.

Clinically observed effects of HF drug regimens like nitroglycerin and ACE inhibitors exhibit their positive effects in the treatment of HF in part through an increase in splanchnic capacitance subsequently shifting blood into the venous reservoir thereby lowering left ventricular diastolic pressure.

An orthostatic stress test (tilt test) can help to distinguish low vascular capacitance from normal. Orthostatic stress causes blood shifts from the stressed volume into the unstressed volume. Veins of the extremities are less compliant than splanchnic veins, and therefore, their role as blood volume reservoir is relatively minimal. Less known is that during body tilt or standing up blood goes mostly into the splanchnic compartment, which results in a decreased preload to the right and left heart. Stimulation of the atrial and carotid baroreceptors results in an increased sympathetic tone causing splanchnic vasoconstriction. This compensatory mechanism is important, as it can rapidly shift volume from the unstressed compartment into active circulation. The hemodynamic response to tilt in chronic HF is atypical, as there is no significant peripheral pooling in the upright posture. It is assumed that the reduced capacitance of the splanchnic compartment serves as a marker of sympathetic tone to the splanchnic vasculature.

Acute oral or intravenous fluid challenge can also serve as a test of splanchnic vascular capacitance. The vascular capacitance determines how "full" the unstressed volume reservoir (venous reservoir) is and how much more fluid can be taken up to it in order to buffer the increase in effective circulation (stressed volume). A fluid challenge could test the capacitance by measuring the effects of a fluid bolus given via an I.V. infusion on cardiac filling pressures.

Patients with a "full tank", (low capacitance of venous reservoir), will not be able to buffer the hemodynamic effects of the fluid bolus as well as patients with a high capacitance in the venous reservoir. This will manifest in a bigger blood pressure increase for the same added volume. Thus patients with HF, HFpEF and patients with increased SNA will be more likely to respond to the fluid challenge with a disproportional rise in cardiac filling pressures. This could serve as a patient selection tool as well as measure of therapeutic success.

To target the splanchnic nerves, primarily the greater splanchnic nerve (GSN) and the thoracic sympathetic trunk and celiac plexus, several invasive and minimally-invasive methods can be used. Although not limited to these methods, access can be transthoracic, transabdominal, percutaneous, transvascular or transvenous. Transvascular access utilizes both vessels of the venous and arterial system, while a transvenous method accesses the nerve structures through the venous network of the cardiovascular system and is envisioned in at least the following vessels: azygos/hemiazygos vein, intercostal veins, vena cava, adrenal vein, phrenic vein, and portal vein.

Tools for catheter navigation include use of extravascular landmarks such as intercostal space and/or vertebrae. Internal scans or detection methods may include fluoroscopic detection of radiographic landmarks, CT scans, MRI and/or ultrasound. These scans would be used for direct nerve visualization, or visualization of adjacent vascular (e.g. azygos) and non-vascular structures (diaphragm, vertebrae, ribs). The use of radiocontrast and a guide wire can aid in the placement of the ablation element of the device.

At the targeted site, some proposed methods of target modulation, specifically to ablate a target nerve include cryo or high temperature based ablation, local drug delivery (e.g. local injection and infiltration by neurolitics, sympatholytics, neurotoxins), local anesthetics, or energy delivery that could include radio frequency (RF) ablation, ultrasound energy delivery, or mechanical compression.

In light of the foregoing, it is desired that the present invention provide treatment that is used in the cardiac catheterization laboratory to ablate a splanchnic nerve such as a greater splanchnic nerve unilaterally on the right or left side of the body or bilaterally on both sides to mobilize blood out of the effective circulation (stressed volume) and shift it into splanchnic organs or vasculature, and splanchnic vascular bed (venous reservoir) in order to moderately decrease and normalize cardiac preload, reduce venous congestion, relieve pulmonary congestion, reduce pulmonary blood pressures and thus sensation of dyspnea and to increase or relatively maintain stroke volume, enhance blood circulation and improve overall heart function. As such, use of the present invention would grant patients suffering from heart disease a return to a higher quality of living and may prevent hospital admissions with ADHF.

Further, the present invention could be used in the therapy of acute as well as chronic HF decompensation. Acute HF decompensation would be prevented or its progression halted by an offloading of the stressed volume and relieving venous congestion, which is the main component of the renal dysfunction in HF. The invention can be used in support of traditional medical therapy like diuretics as it can interrupt or delay progression of cardiac decompensation. Said offloading of the stressed volume and relieving venous congestion can be expected to increase diuretic responsiveness of the patients.

In a chronic CHF state, the invention can be used on a long-term basis to improve fluid distribution, increase capacitance, relieve venous congestion, improve relaxation of ventricles and thus improve symptoms of congestion like shortness of breath and improve exercise capacity.

Compared to present methods of nerve ablation, the invention aims to create a reliable and consistent method of targeted selective GSN ablation that is safe and causes no adverse effects such as pain, serious long term damage to gastric function, sensation or other unintended, untargeted nerve damage.

Additionally, the present invention fulfills a long desired need to provide a treatment for HF, especially for patients of diastolic or HFpEF and particularly a need to reduce pulmonary artery blood pressure and relieve dyspnea (shortness of breath) in response to exercise and in some cases at rest.

BRIEF DESCRIPTION OF THE DRAWINGS

Other advantages of this invention are made apparent in the following descriptions taken in conjunction with the provided drawings wherein are set forth, by way of illustration and example, certain exemplary embodiments of the present invention wherein:

FIGS. 19A to 19D are graphs illustrating responses of the patient to the blocking of a nerve.

DETAILED DESCRIPTION OF THE INVENTION

The present invention relates to a medical device and method that offers treatment of heart disease, dysfunction and heart failure, particularly HFpEF through the mechanism of increased venous capacitance and relief of pulmonary congestion and increased diuretic responsiveness. This treatment is provided through ablation of at least a portion of a splanchnic nerve (e.g., greater splanchnic nerve or lesser splanchnic nerve) with a catheter delivered to a vessel (e.g. azygos or hemiazygos vein or intercostal vein) to impede or stop communication of a nerve signal along the ablated nerve, which can affect physiological responses that are directly or indirectly involved in the numerous factors of cardiovascular health.

One preferred embodiment comprises a catheter delivered through a patient's vascular system to an azygos or hemiazygos vein and their branches for ablating a portion of a right or left greater splanchnic nerve. The catheter may comprise an ablation element (e.g., RF electrodes, cryogenic applicator, chemical agent delivery needle, ultrasound transducer, laser emitter), and a means to confirm proximity to target nerve, such as a greater splanchnic nerve, or non-target neural structures (e.g., electrical stimulation or blocking electrodes, cryogenic applicator, chemical agent delivery needle, visual aids such as radiopaque or echogenic markers). The catheter may be used as part of a system comprising other components that contribute to the function of the catheter. For example, the system may comprise an ablation energy source (e.g., RF signal generator, cryo console, ultrasound signal generator, chemical agent source or pump, laser generator), a controller, or a computerized user interface. To ablate a portion of a target nerve, the ablation energy source delivers ablation energy from an ablation element positioned in a patient's blood vessel (e.g. azygos, intercostal or hemiazygos vein) proximate the target nerve. The ablation energy passes from the ablation element to the target nerve. To confirm proximity to a target or non-target neural structures a stimulating agent, such as electric field or a drug known to activate sympathetic nerves, may be delivered to temporarily activate or block nerve activity and a physiological response may be observed or monitored for correlation to the nerve stimulation or block. Similarly, success of ablation may be confirmed by electric stimulation of the target nerve and observing the physiologic response, changes in the physiologic response compared to pre-ablation or absence of physiologic response where one is expected.

Physiology

Figure 1:
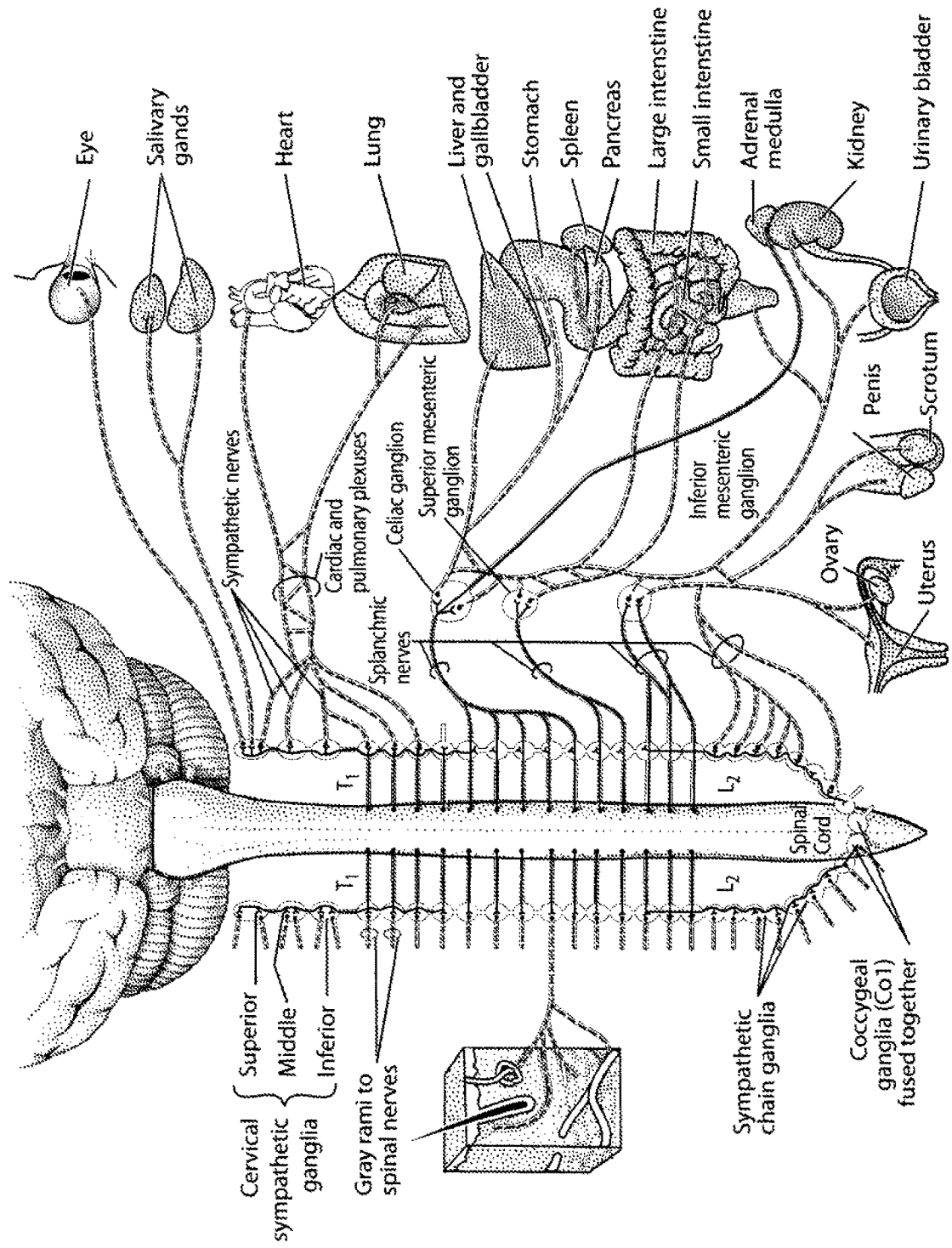
FIG. 1 is an anatomical representation of the supply of sympathetic nerve fibers to organs of the human body.

FIG. 1 is an anatomical representation of the supply of sympathetic nerve fibers to organs of the human body. The SNS is part of the autonomic nervous system, which also includes the parasympathetic nervous system.

The SNS activates what is often termed the fight or flight response. Like other parts of the nervous system, the sympathetic nervous system operates through a series of interconnected neurons. Sympathetic neurons are frequently considered part of the peripheral nervous system, although there are many that lie within the central nervous system.

Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through chemical synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation can elicit the release of adrenaline from the adrenal medulla.

Once released, noradrenaline and adrenaline bind adrenergic receptors on peripheral tissues. Binding to adrenergic receptors causes the effects seen during the fight-or-flight response. These include pupil dilation, increased sweating, increased heart rate, and increased blood pressure.

Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Thoracic splanchnic nerves (e.g., greater, lesser, or least splanchnic nerves), which synapse in the prevertebral ganglia are of particular interest for this invention.

Figure 2:
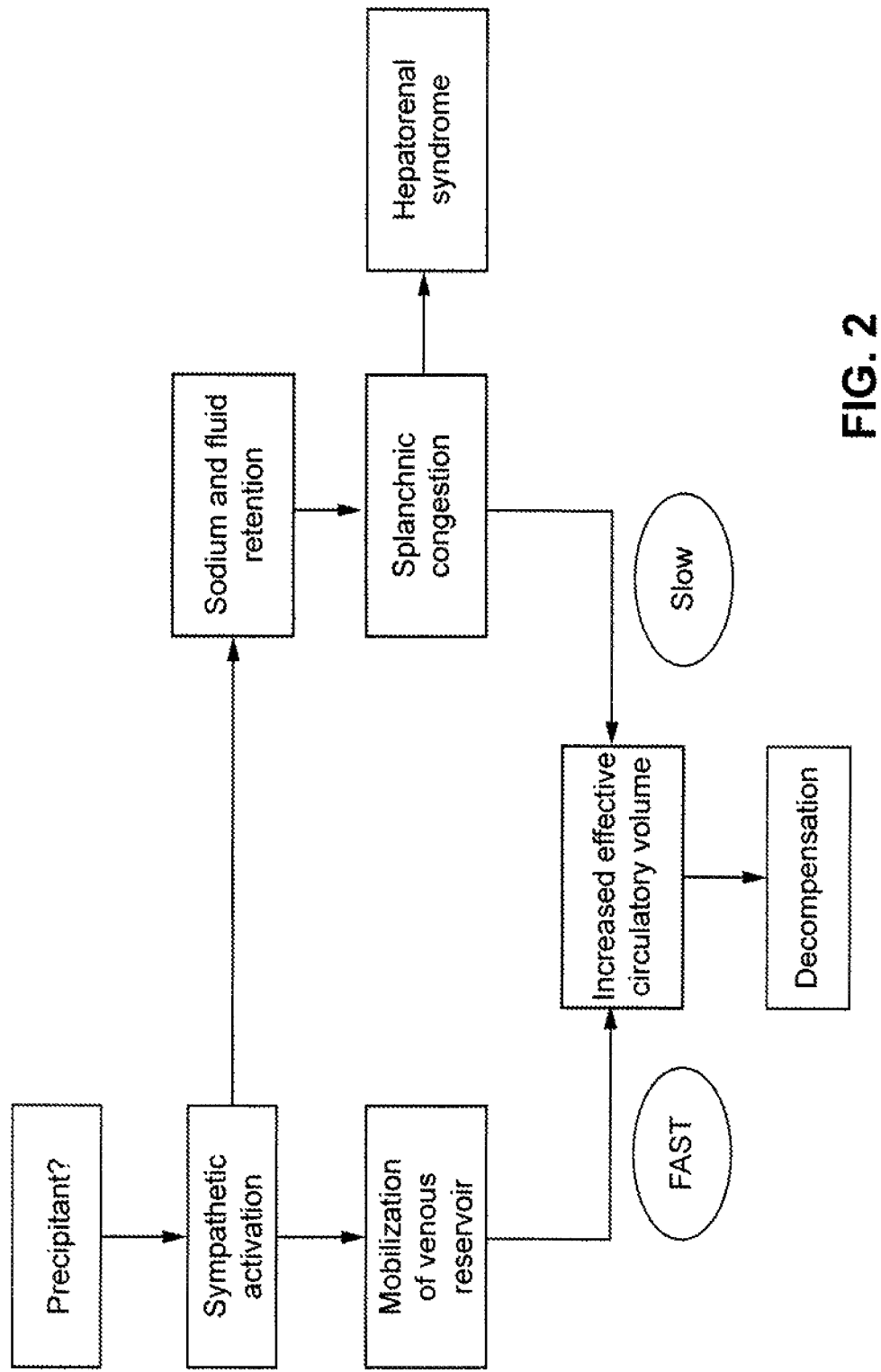
FIG. 2 is a flow diagram showing the mechanisms of decompensated heart failure

FIG. 2 is a flow diagram showing the mechanisms of decompensated heart failure. It illustrates the role of sympathetic nerve activation in the mobilization of venous reservoir into the effective circulatory volume leading to decompensation. Reversing, at least partially, by ablation of a greater splanchnic nerve, the sympathetic activation of splanchnic nerves is expected to relieve HF symptoms and reduce load on the failing heart.

A particular area of interest in the body is the splanchnic compartment, splanchnic vascular bed, or splanchnic reservoir, which include the vasculature of the visceral organs including the liver, spleen, small and large bowel, stomach as well as the pancreas. The splanchnic venous vascular bed serves as the major blood reservoir and can be affected by activation (e.g., stimulation) or deactivation (e.g., blocking or ablation) of splanchnic nerves and particularly of the greater splanchnic nerve (GSN) causing mobilization, release or uptake of venous blood from or to splanchnic vascular beds, respectively, and important changes in circulating blood volume.

The GSN may at least partially control splanchnic venous capacitance. Capacitance is reduced in CHF patients and particularly in some very hard to treat HFpEF patients as a part of overall elevated sympathetic state. The sympathetic fibers in the greater splanchnic nerve bundle that control contraction of splanchnic veins are the particular target of the proposed ablation therapy. In the context of this invention the GSN can mean right or left greater splanchnic nerve and transvenous ablation and stimulation can be performed from the azygos vein to access the right greater splanchnic nerve, or from the hemiazygos vein to access the left greater splanchnic nerve, or from their respective tributaries (e.g. right or left intercostal veins) or a bilateral treatment can be performed from both the azygos and hemiazygos to access both right and left greater splanchnic nerves.

The splanchnic congestion and high venous pressure is believed to adversely affect renal function and as illustrated by hepatorenal syndrome that causes diuretic resistance. It is believed by inventors that the proposed ablation may reverse this phenomenon, improve renal function and enable diuretics to work (restore diuretic responsiveness).

Figure 3:
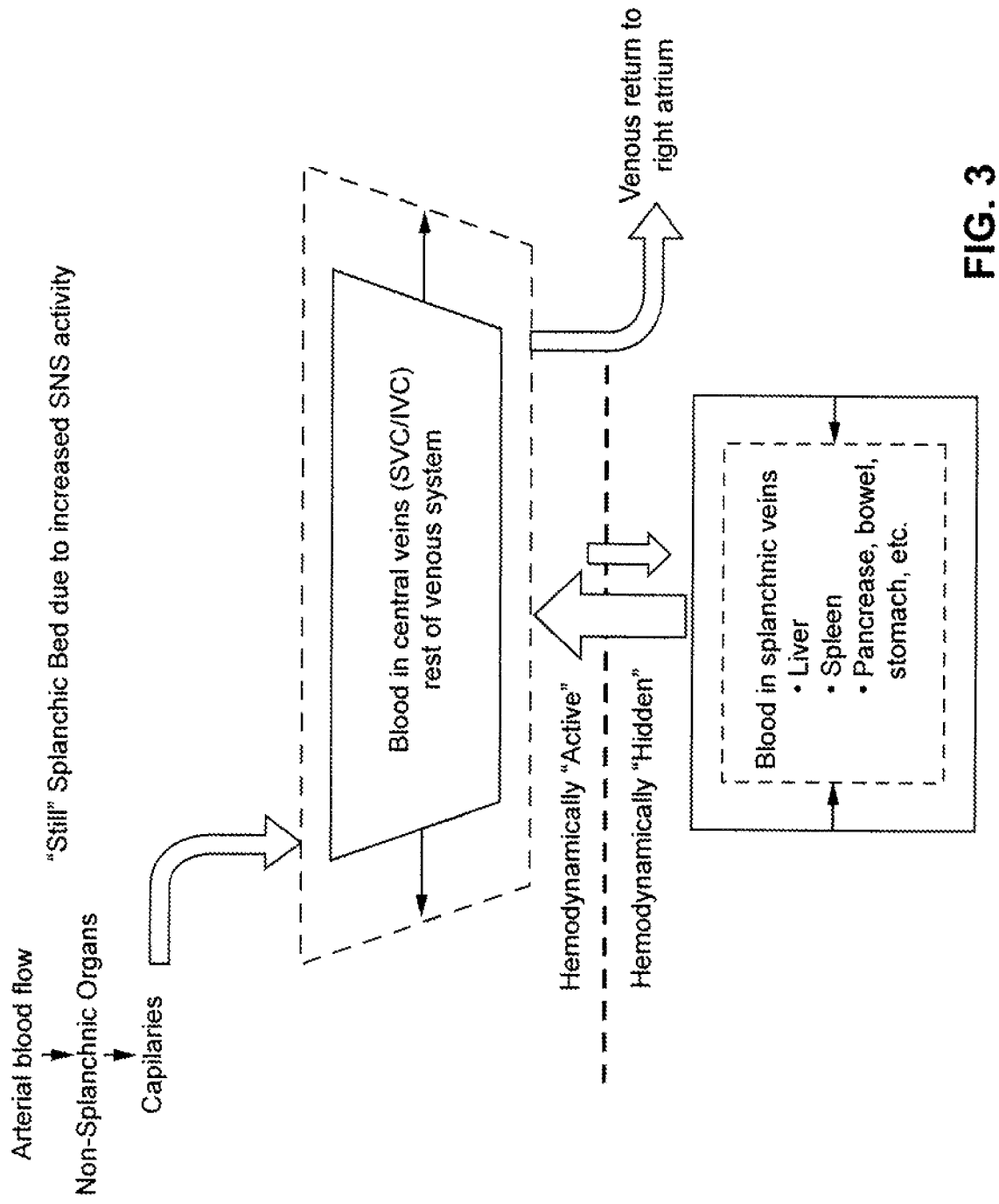
FIG. 3 is a partial flow diagram showing the role of splanchnic compartment in blood volume distribution in heart failure.
Figure 4:
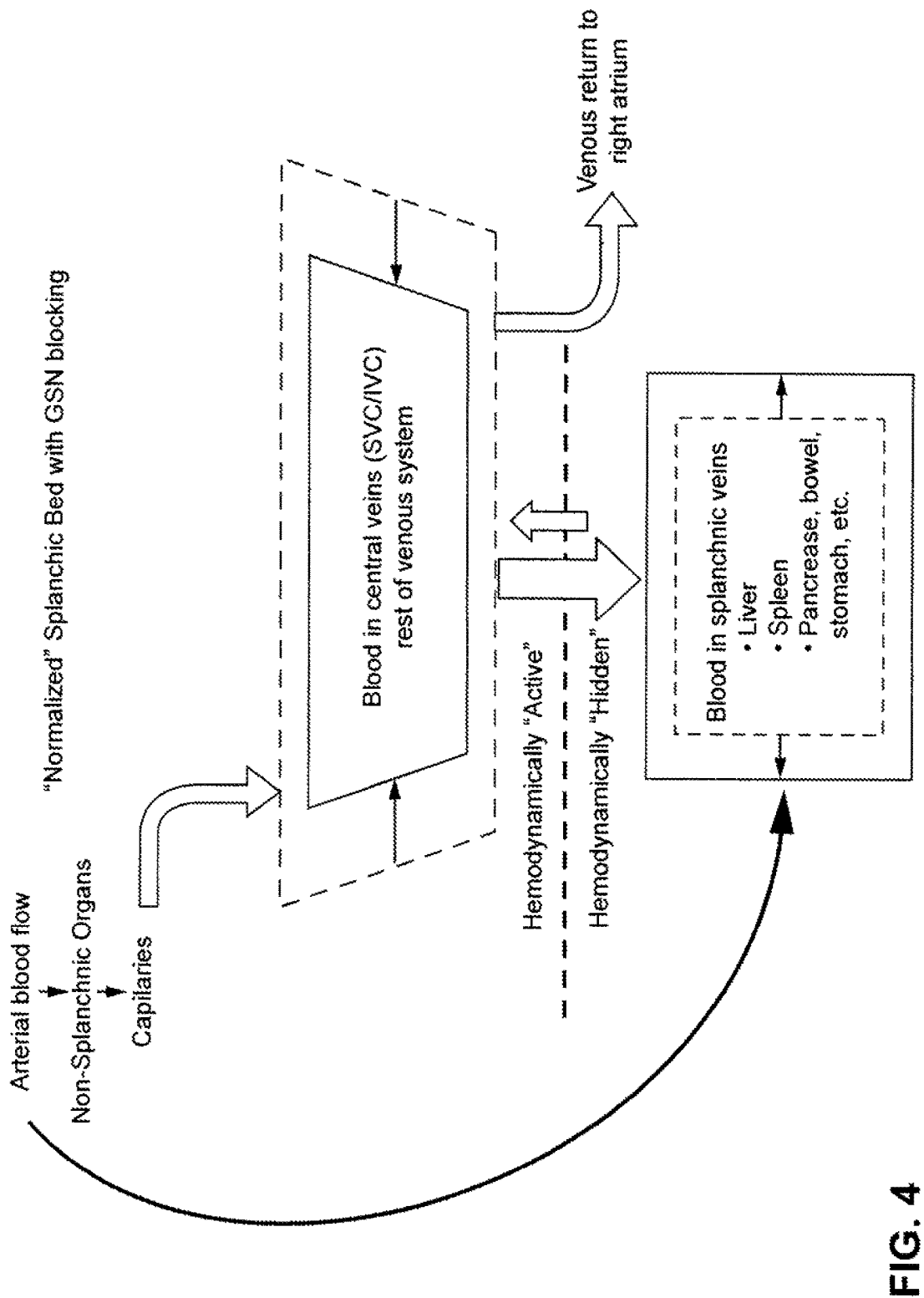
FIG. 4 is a partial flow diagram showing the role of the therapeutic effects of invention to heart failure.

FIG. 3 and FIG. 4 show some of the interactions between increases in sympathetic nervous system activity, including natural firing of the GSN, and the storage of blood in the splanchnic bed. As illustrated by FIG. 3, increased central SNA, can manifest, at least partially, in the elevated activity of the GSN in all types of HF, resulting in a lower splanchnic capacitance and possibly stiffened, less-compliant splanchnic bed and regional effects including a decrease in the amount of blood stored in the splanchnic veins perfusing and surrounding the splanchnic organs (e.g., liver, spleen, pancreas, stomach, bowels) and an increase in the amount of blood in central veins. The volume of blood in splanchnic veins or the splanchnic vascular bed can be described as a "venous reservoir", or "unstressed volume" and refers to the blood volume that does not contribute to the effective circulating volume and is therefore hidden from circulation or the hemodynamically hidden blood volume. The volume of blood in central veins can be termed "effective circulatory volume" or "stressed volume" and refers to blood that is present mainly in the non-splanchnic veins and is one of the main determinants of preload to the heart and in CHF can contribute to venous congestion, high pulmonary circulation pressures and sensation of dyspnea.

Conversely, as illustrated by FIG. 4 the compliance of the splanchnic bed can be relaxed or normalized from the "stiff" of contracted state by decreased sympathetic nervous system activity. Ablating a splanchnic nerve (e.g. GSN, lesser splanchnic nerve, least splanchnic nerve) can result in a decrease of efferent sympathetic tone to smooth muscle in the walls of veins in the splanchnic vascular bed referred to as splanchnic "venodilation" or in the overall decrease in sympathetic nervous system activity. Understanding and utilizing these interactions are some of the primary aims of several of the exemplary embodiments of the present invention. Specifically, the capacitance of splanchnic vasculature is desired to be increased.

Figure 5:
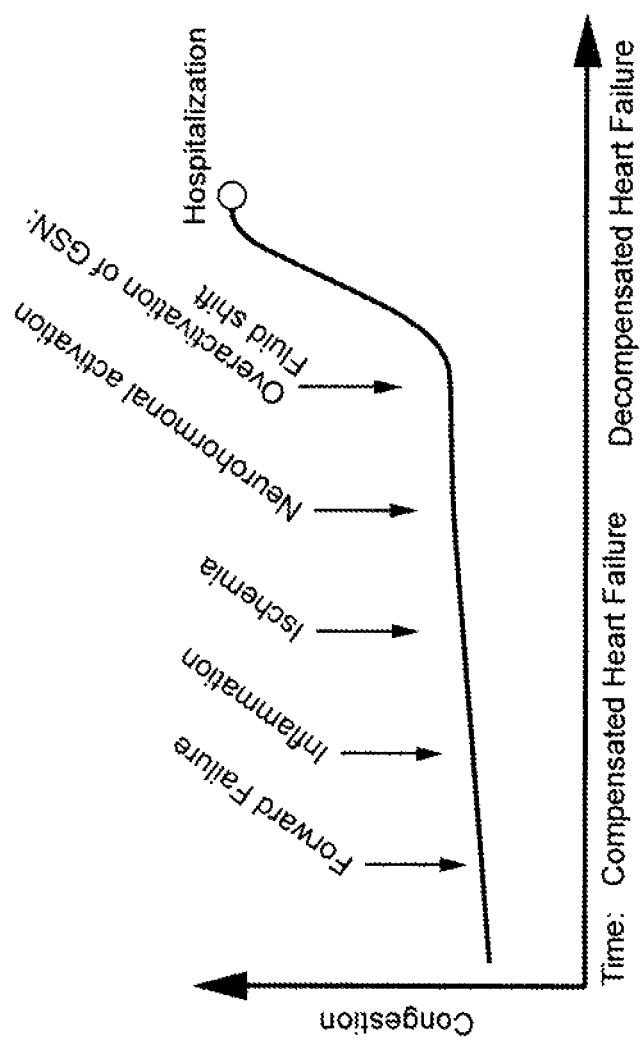
FIG. 5 is a graphical representation of pathophysiology of acute decompensated heart failure.

FIG. 5 shows one possible clinical scenario in which the sympathetic hyperactivity of the greater splanchnic nerve leads to the acceleration of fluid overload and pulmonary venous congestion in an HFpEF patient.

Endovascular Ablation

Endovascular nerve ablation, or ablation of neural structures using a catheter delivered through a blood vessel, particularly deep visceral nerves that are near the blood vessel (e.g., less than about 5 mm from an internal vessel wall), may be advantageous over surgical resection or ablation. For example, endovascular ablation may be less invasive, be faster procedurally, and have faster patient recovery. It may be beneficial to use a patient's venous system to deliver ablation energy since interventions in veins are considered safer than in arteries. Blood pressure in a vein is lower and limits risk of bleeding and debris or clot from ablation is safer since veins terminate in the lungs that act as a natural blood filter. It is also advantageous that veins are more elastic and can be occluded and stretched in order to achieve better fixation and apposition of the ablating device in relation to the nerve. Specifically, in the case of an azygos or hemiazygos vein there is large redundancy in the venous system and occlusion of the azygos vein is not dangerous to the patient.

There are several accepted methods of ablating a nerve through a wall of a blood vessel such as RF ablation using resistive heating, cryo-ablation using cold, ultrasound heating ablation, and injection of neurolytic blocking agent (e.g., form of nerve block involving the deliberate injury of a nerve by the application of chemicals, in which case the procedure is called "neurolysis") in which chemicals such as alcohol or more specifically acting sympatholytic agents like guanethidine, botox (i.e., botulinum toxin A) and others can be applicable.

A method and device for ablating a greater splanchnic nerve using an ablation catheter placed in an azygos vein may be configured to safely avoid important non-target nerves and structures. For example, the celiac ganglion is near the greater splanchnic nerve. Placement of an ablation element that creates, for example, a 5 mm diameter lesion that permanently destroys the GSN where it is in close proximity of the azygos vein at or slightly above the diaphragm will protect the celiac ganglion from ablation. Celiac ganglia are located in the abdominal cavity just below the diaphragm. Other non-target nerves may include lesser and least splanchnic nerves. Thus a targeted selective ablation of nerves is possible to suite needs of different groups of patients with HF.

Figure 6:
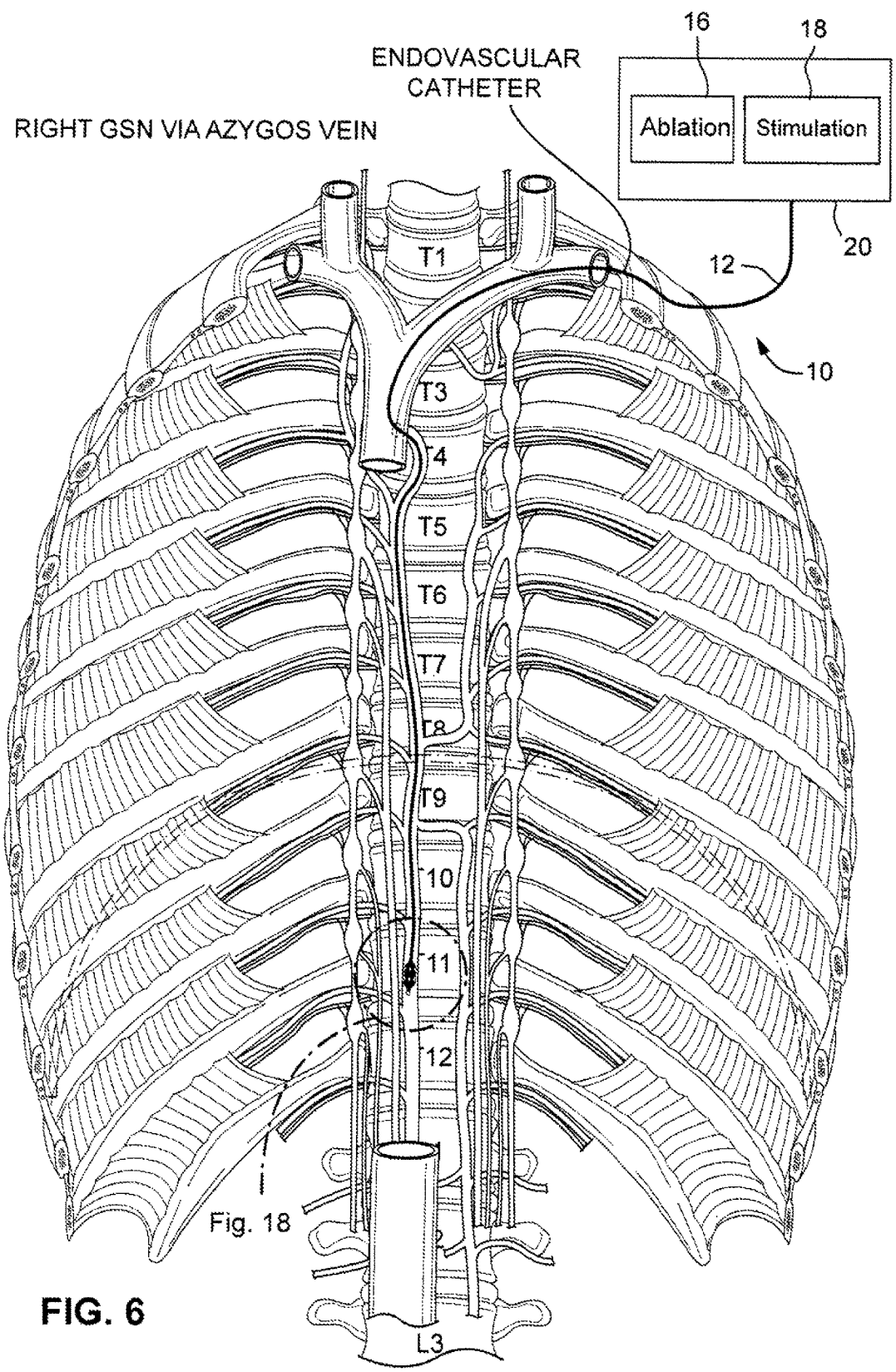
FIG. 6 is an anatomical representation showing azygos vein catheterization for right GSN ablation with an intravenous catheter suitable for stimulation and ablation.
Figure 7:
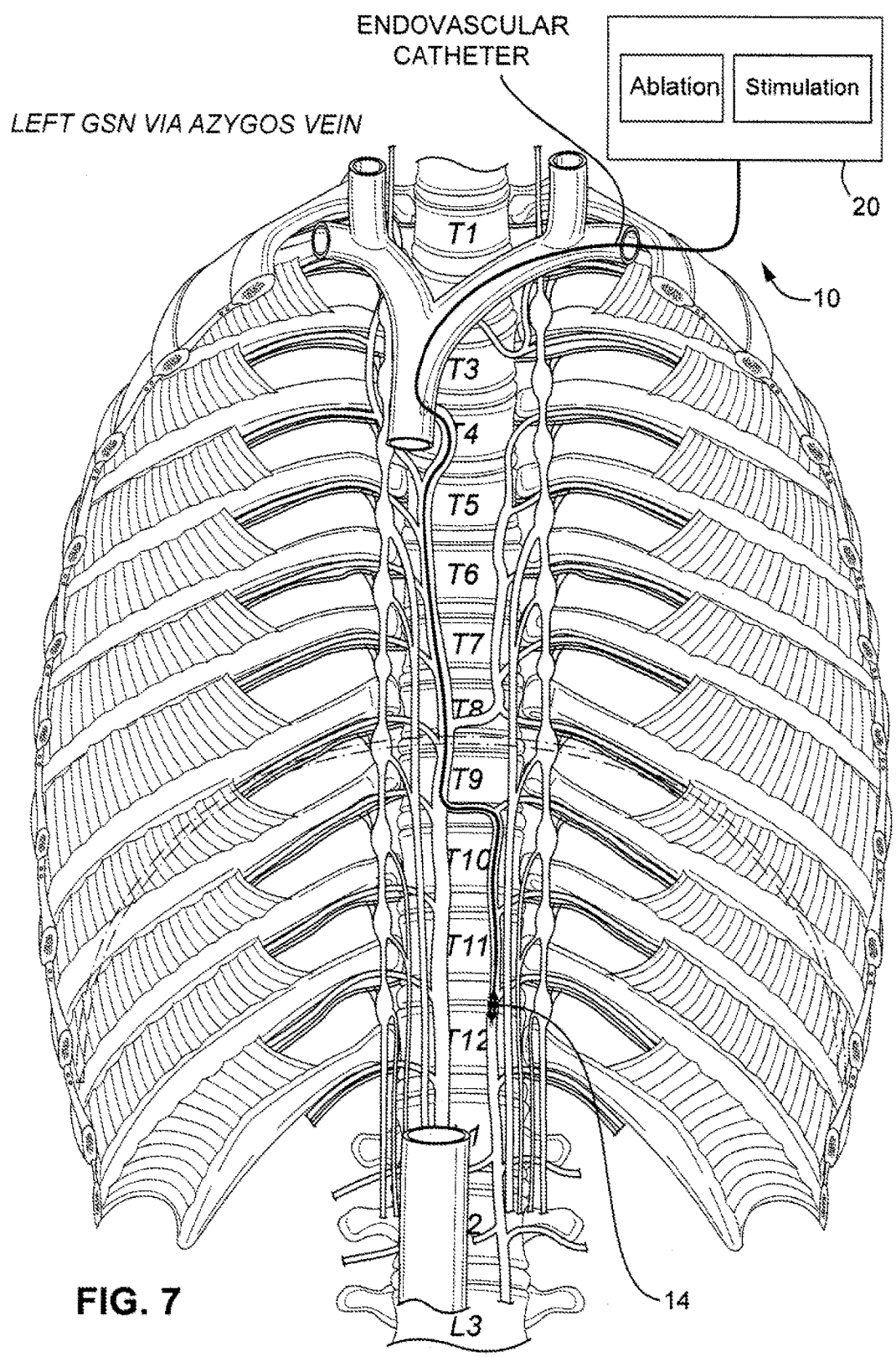
FIG. 7 is an anatomical representation showing the azygos vein catheterization for left GSN ablation with an intravenous catheter suitable for stimulation and ablation.

FIG. 6 shows an example of a catheterization approach from a left subclavian vein to a suitable position in an azygos vein for right GSN ablation. FIG. 7 shows an example of a catheterization approach from the left subclavian vein to a suitable position in a hemiazygos vein for left GSN ablation by crossing over from azygos to hemiazygos vein. Endovascular approaches to the azygos vein may comprise introduction into the vascular system, for example, at the radial, brachial, subclavian, jugular or femoral veins.

A guidewire may facilitate advancement of a catheter 10 through tortuous vessel pathways. The catheter may include an extended tubular member 12 including lumens, such as for the guidewire for injection of drugs and radiocontrast. Both bilateral and unilateral, left and right GSN ablation is possible and may be desired based on the patient's anatomy and responses to diagnostic stimulation.

Figure 8:
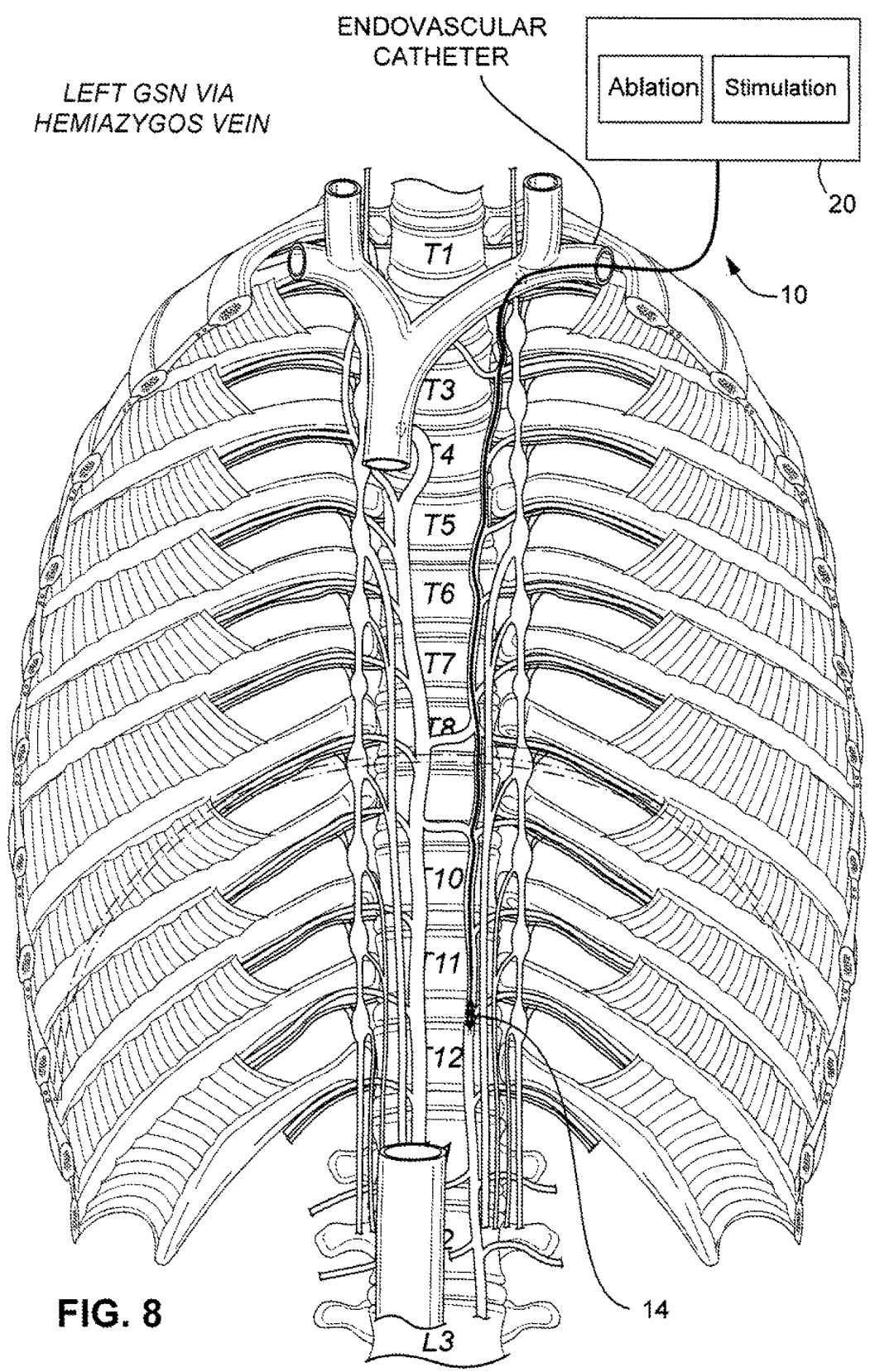
FIG. 8 is an anatomical representation showing the hemiazygos vein catheterization for left GSN ablation with an intravenous catheter suitable for stimulation and ablation.
Figure 9:
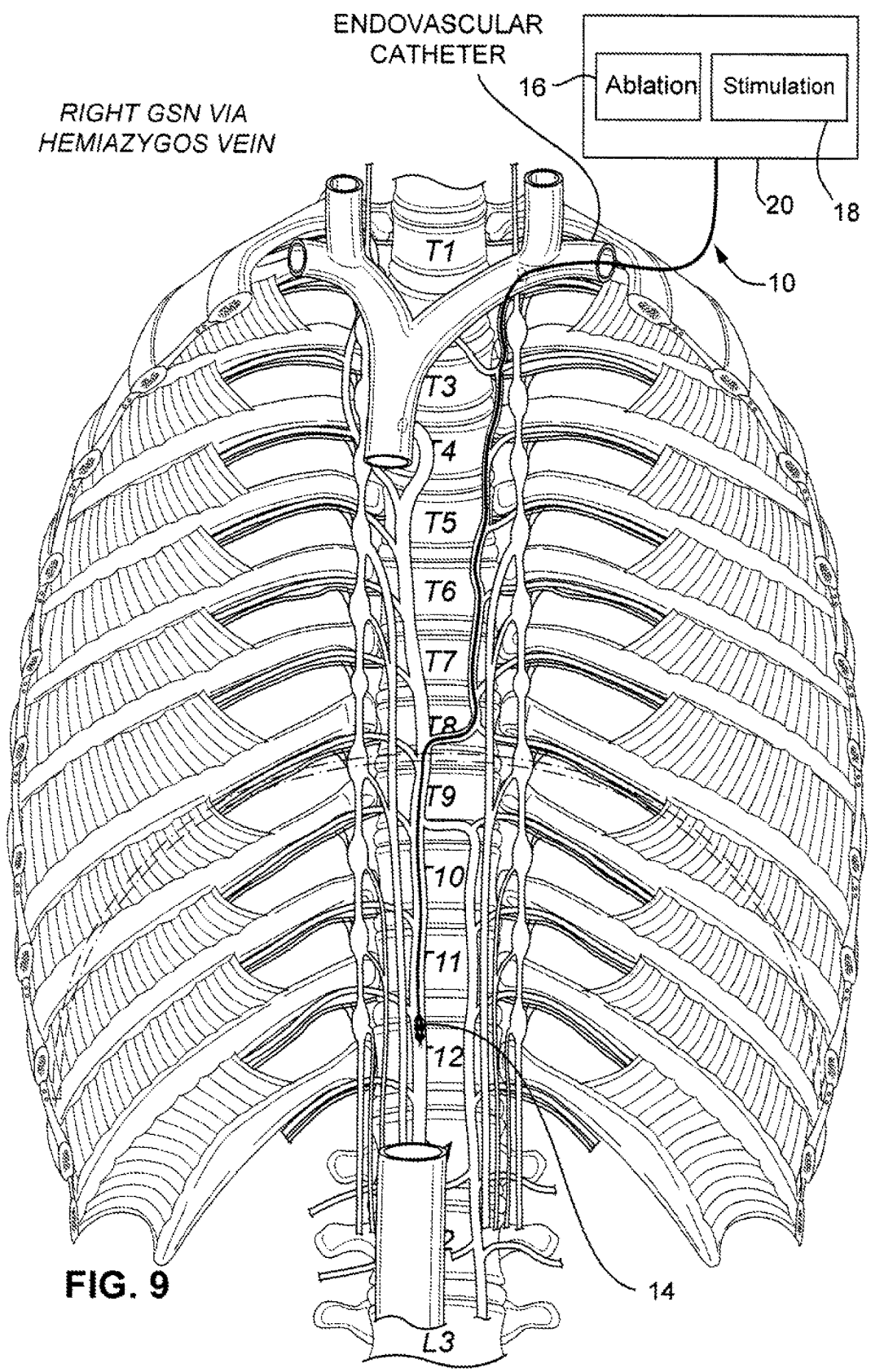
FIG. 9 is an anatomical representation showing the hemiazygos vein catheterization for right GSN ablation with an intravenous catheter suitable for stimulation and ablation.

Approaches to identify the best location (mapping) and target as well as the best approach to GSN ablation are shown in FIGS. 8 and 9. These figures show examples of a catheterization approach from a left subclavian vein to a suitable position in a hemiazygos vein for left and right GSN ablation, respectively.

The catheters in FIGS. 6 to 10 may each comprise at least one ablation element 14, 22 to deliver ablation therapy as well as at least one electrical stimulation element to confirm proximity to a target nerve, such as a GSN, or non-target neural structures. The catheter in each of FIGS. 6 to 10 may be used as part of a system comprising other components that contribute to the function of the catheter. The system may comprise an ablation energy source 16 (e.g, RF signal generator, cryo console, ultrasound signal generator, chemical agent source or pump, laser generator), an electrical stimulation energy source and a computer controller 18 with embedded logic and software and a user interface with manual controls and displays. A console 20 may house the ablation energy source, the electrical stimulation energy source, the computer controller, user interface and displays.

Figure 10:
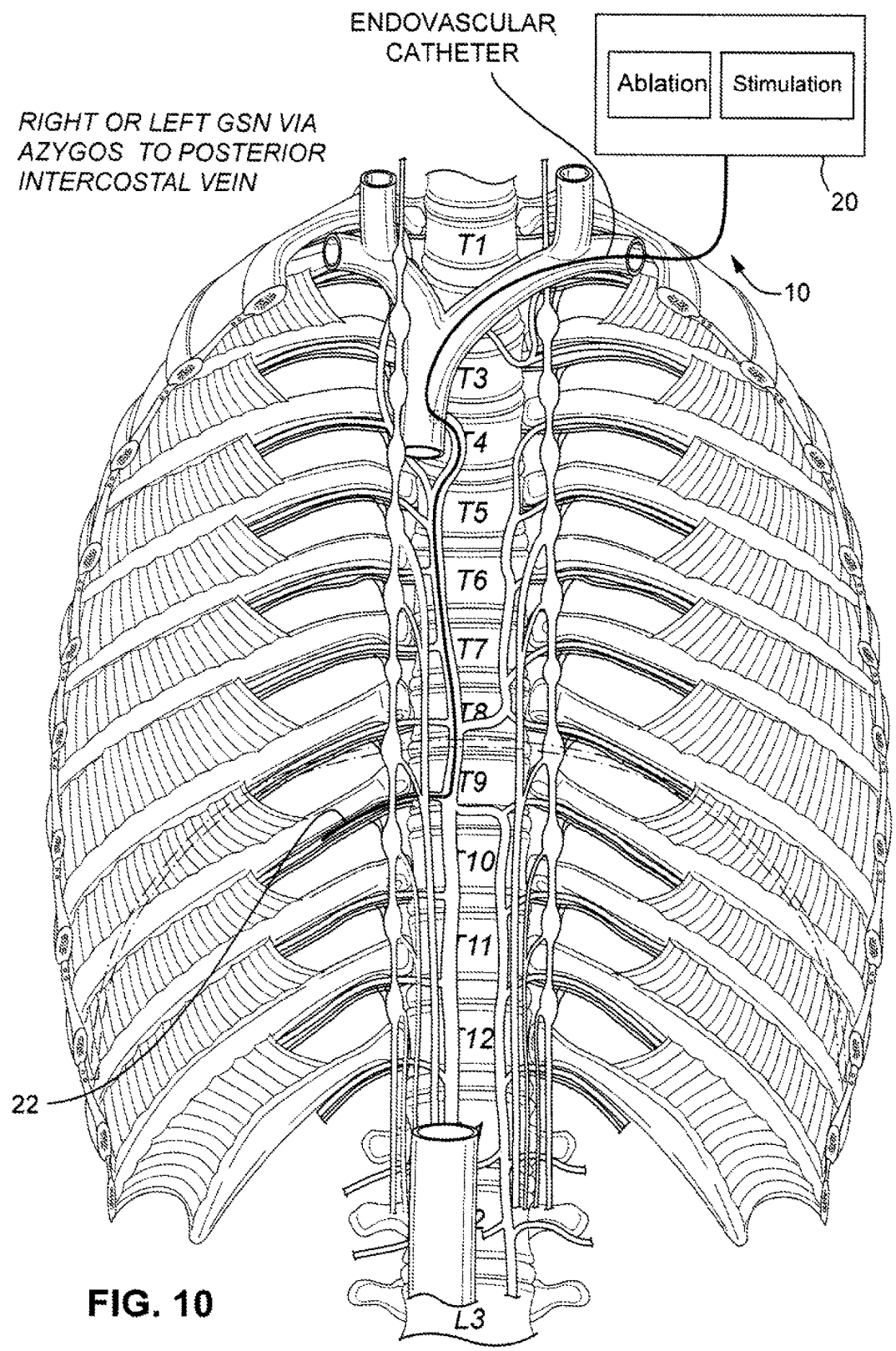
FIG. 10 is an anatomical representation showing left GSN catheterization via the azygos vein to posterior intercostal vein.

In an embodiment of the invention, as shown in FIG. 10, ablation and stimulation elements on a catheter are positioned in an intercostal vein near a GSN and sympathetic chain. The ablation and stimulation elements can be electrodes.

The catheterization approach used in this example is the one from a left subclavian vein via the azygous vein into the posterior intercostal vein. Other approaches are possible through suitable veins. The catheter may comprise at least one ablation element to deliver ablation therapy and at least one electrical stimulation element to confirm proximity to a target nerve, such as a GSN, or non-target neural structures. The catheter may be used as part of a system comprising other components that contribute to the function of the catheter. The system may comprise an ablation energy source, an electrical stimulation controller, or a user interface. Additional elements such as monitoring of temperature and impedance of tissue can be added to improve performance and safety of the ablation system.

Figure 11:
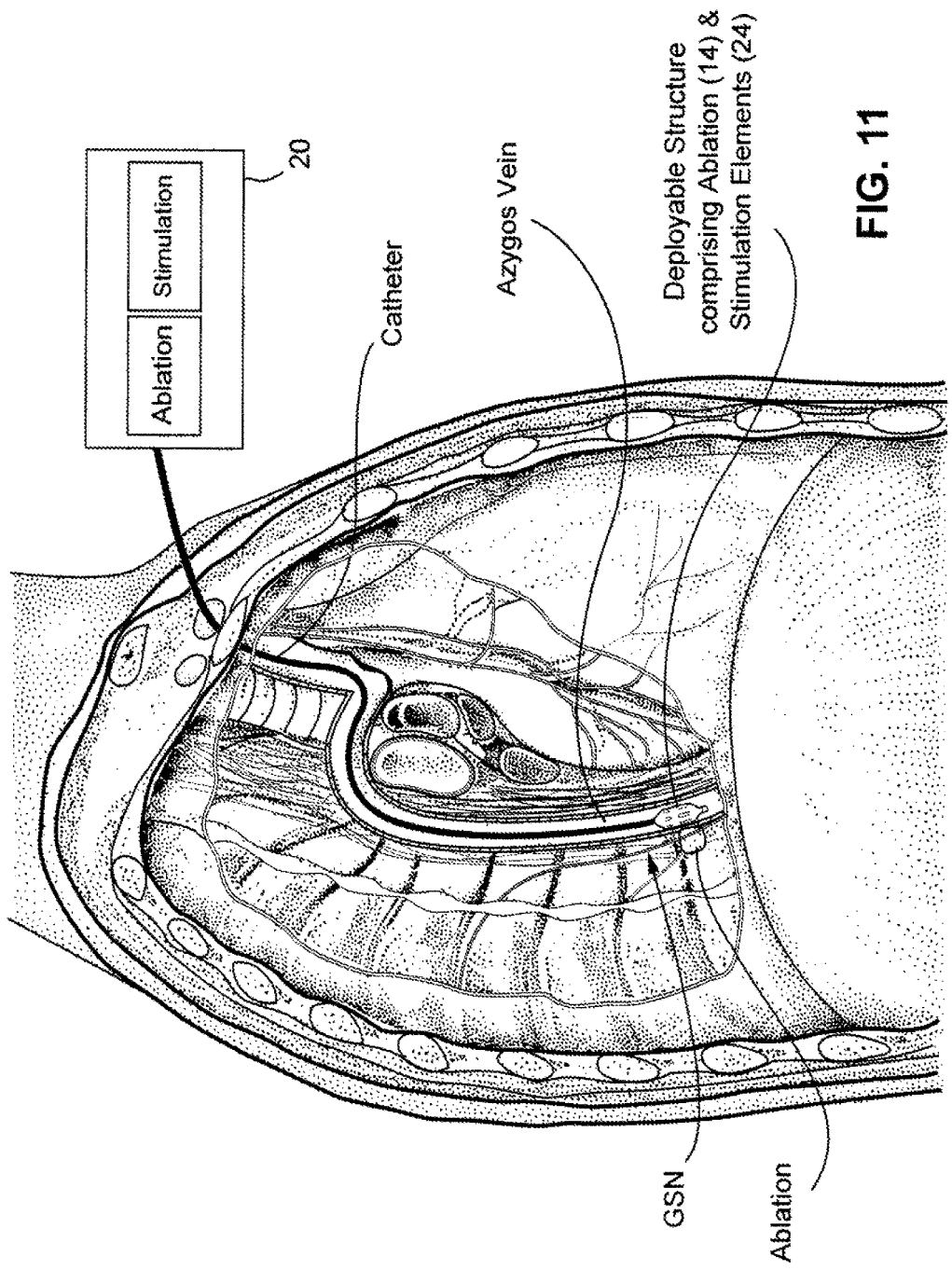
FIG. 11 is an anatomical representation showing the azygous vein and greater splanchnic nerve and their proximity, which allows for a transvenous approach with an intravenous catheter deployable structure suitable for stimulation and ablation.

In an embodiment of the invention, as illustrated in FIG. 11, an ablation element on a catheter is positioned in an azygos vein near a greater splanchnic nerve. The catheter may comprise a deployable structure positioned at its distal region. The deployable structure comprises at least one ablation element (e.g., RF electrode) that is placed in apposition with the azygos or hemiazygos vein wall when the deployable structure is expanded. The deployable structure may be a balloon, a cage, a basket, a preformed shape such as a lasso or loop. The deployable structure may further comprise at least one stimulation element 24 (e.g., electrical stimulation cathode and optionally anode), or a visualization aid (e.g., radiopaque marker, contrast delivery lumen). The azygos (and hemiazygos) veins which run up the right and left sides of the thoracic vertebral column drain towards the superior vena cava, in part within the thoracic cavity. Intravenous access via the azygos vein allows for the catheter to access an area in proximity to the thoracic splanchnic nerves, in particular, the greater splanchnic nerve (GSN).

Experiments in animals and human cadavers where performed in which the GSN was successfully accessed with a catheter advanced to an azygos vein at the level of the diaphragm wherein an electrode was positioned close enough to electrically stimulate and potentially ablate the greater splanchnic nerve. In animals experiments GSN access was performed on the right side. This was confirmed by observing hemodynamic effects of greater splanchnic nerve stimulation with electric pulses applied from the azygos vein. Inventors also performed experiments where the GSN was surgically accessed, visualized, stimulated with a nerve cuff and later resected. Consistent and similar hemodynamic effects that suggested therapeutic possibilities were observed.

Stimulation Confirmation Embodiments

Regardless of the modality of ablation, embodiments of a device and method may further be configured to assist the ablation procedure with a means to confirm safety and efficacy prior to and following an ablation step. A means to confirm safety may comprise detection of a non-target nerve or structure or absence thereof within a range of ablation energy delivery. A means to confirm technical efficacy may comprise detection of a target nerve within range of ablation energy delivery before an ablation step and absence of a target nerve signal transmission following the ablation step. A means to confirm procedural efficacy may comprise temporarily blocking a target nerve to assess if a resulting physiologic response is representative of a desired clinical effect of the procedure.

To facilitate a technically effective procedure, an embodiment may involve confirming that the ablation lesion will be created in a desired location and that a targeted nerve is sufficiently within range of ablation energy delivery before ablation energy is delivered to cause irreversible damage to the target nerve or potentially to an untargeted area. This may be achieved by delivering an electrical stimulating signal from at least one stimulating electrode to excite nerves in proximity to the stimulating electrode and observing a physiologic effect such as hemodynamic changes. The stimulating electrodes may be a pair of electrodes constituting an anode and cathode, a single monopolar electrode communicating with a dispersive electrode, the same component that is used to deliver an electrical ablation energy such as radiofrequency or electroporation, or a distinct electrode or pair of electrodes positioned appropriately relative to an ablation element.

Figure 12:
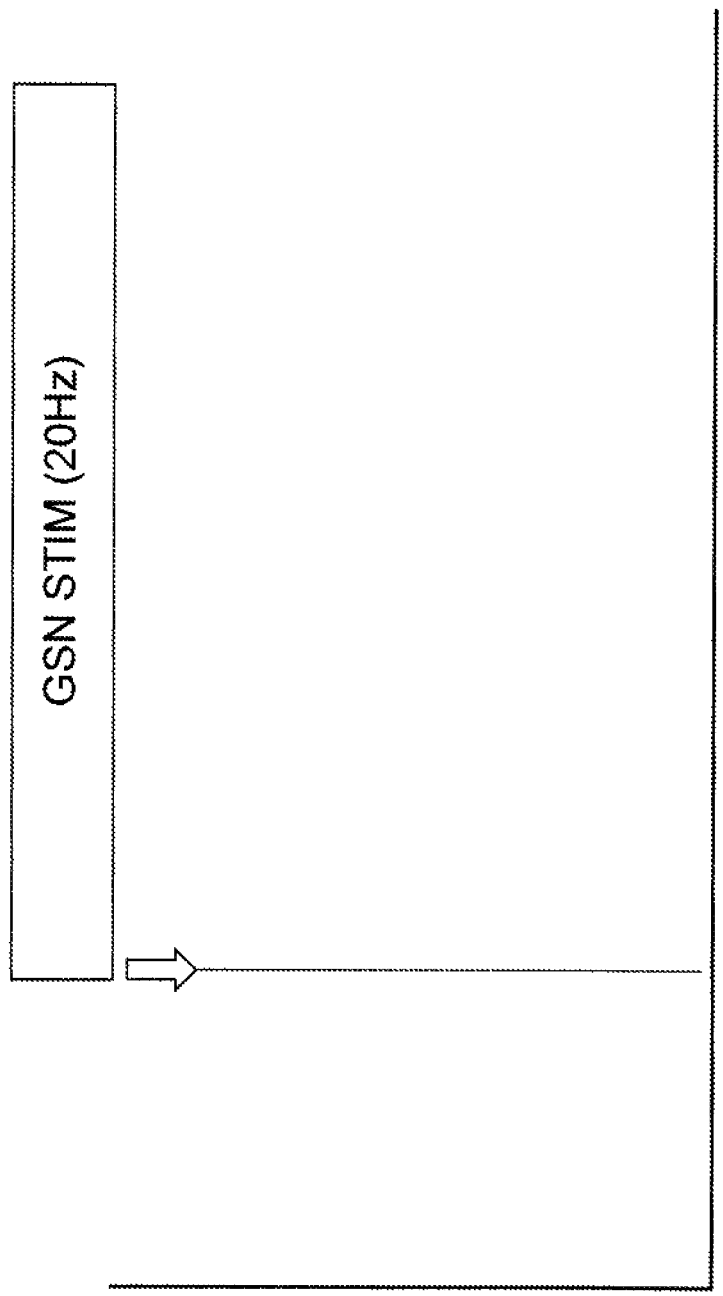
FIG. 12 is a plot of aortic and ventricular pressure in response to electrical stimulation of a GSN in an animal study.

FIG. 12 illustrates a response to stimulation of a GSN at the level just above the diaphragm in an animal experiment performed by the inventors. The recognizable waveforms of aortic and left ventricular pressure reflect the physiologic response to stimulus. Similar increases were observed in central venous pressure, right atrial pressure and pulmonary artery pressure that can be measured and monitored in real time in any well-equipped modern catheterization laboratory by a trained cardiologist.

In an embodiment wherein a stimulation electrode or pair of electrodes is distinct from an ablation element they may be positioned on the catheter relative to one another so that the stimulation zone (e.g., region in which the stimulation signal delivered by the stimulation electrode is strong enough to elicit an action potential in a nerve) correlates with an ablation zone (e.g., region in which ablation energy delivered by the ablation element is sufficient to cause irreversible or long lasting damage to nerve tissue).

A stimulation signal may be controlled by a computerized console 20 (See FIG. 6-10) and may comprise a signal profile that facilitates confirmation of technically efficacious positioning. The computerized console may include processors accessing non-transitory memory storing instructions that cause the console to generate a stimulation signal. For example, the size of a stimulation zone may be a function of amplitude and a signal profile. The console may achieve the stimulation zone by delivering signal energy by varying amplitude (e.g., linear ramp, stepwise ramp, alternating levels) or frequency of stimulation. An observed response corresponding to a given amplitude may indicate distance of a target nerve to an ablation element, and delivery of ablation energy may be adjusted (e.g., manually or automatically) to create an efficacious ablation zone.

For example a different energy delivery electrode can be selected or the catheter can be repositioned. In another example, a signal profile comprises periods of on and off (e.g., stimulating amplitude(s) and non-stimulating energy levels) in which a physiologic response may follow the signal profile to eliminate false positive or negative assessments.

In an embodiment, a transvenous application of electrical stimulation of a nerve delivering currents of 0.5 to 15 mA, frequency of 1 to 50 Hz and pulse duration of 50 to 500 microseconds may be suitable to test if proximity to the nerve is within about 5 mm. Sedation may be used in order to prevent painful sensation by the patient. If a physiologic response is elicited, the cathode electrode is very likely to be within 1 to 5 mm distance from the target nerve and ablation in that area is likely to destroy the nerve permanently while sparing nerves outside of the ablation zone in embodiments configured to create an ablation zone of about 5 mm. It is estimated that the location closest to the nerve and the corresponding electrode (See FIG. 13) will elicit response at the lowest energy (example of nerve mapping). For example, the ablation element may be an RF electrode (e.g., having an exposed surface area of about 5 to 15 mm$^3$) in monopolar configuration with a dispersive grounding pad on the patient's skin to complete the electrical circuit.

Ablation energy may be radiofrequency electrical current having a frequency in a range of about 350 to 500 kHz and a power in a range of about 5 to 50 W.

The delivery of RF energy may be controlled by an energy delivery module associated with the computer console that uses temperature feedback from a sensor associated with the RF electrode. Observation of a physiologic response may involve equipment for measuring the response (e.g., equipment known in the art for measuring or monitoring hemodynamic parameters such as blood pressure and heart rate, or with sensors associated with the catheter or the system) that provides an indication of the parameter.

Confirmation of efficacious positioning may be assessed manually by a practitioner by observing the parameter measurements in real time. Alternatively confirmation may be assessed automatically by the computerized system console that takes input from the physiologic monitoring equipment and compares it to a stimulation signal profile (automated mapping). The automated mapping or confirmation assessment may further select or assist in selecting an appropriate ablation energy delivery profile.

A catheter may be configured to monitor a physiologic response to nerve stimulation and comprises a blood pressure transducer on the catheter that may be positioned in a blood vessel in addition to an ablation element and a stimulation element. The device or system may further comprise a second blood pressure transducer that may be positioned in a different part of the circulation system (e.g., arterial system such as femoral or radial artery, pulmonary circulation such as pulmonary artery, central venous system such as vena cava or right atrium of the heart or splanchnic circulation or pulmonary circulation system such as in a pulmonary artery) to compare blood pressure measured in different locations and assess changes in response to nerve stimulation.

To facilitate a safe procedure, an embodiment may involve confirming that the ablation lesion will not do irreversible damage to important non-target nerves, such as celiac ganglia or lesser splanchnic nerve, if that is the selected therapy modality, before ablation energy is delivered. This may be achieved by electrically stimulating the adjacent nerves with the same or different electrodes and observing the physiologic (e.g. heart rate or hemodynamic such as blood pressure or flow) effects. An embodiment may utilize the same principles and components as described above wherein a stimulation zone is correlated to an ablation zone however an observed physiologic response may be indicative that an important non-target nerve is stimulated. An undesired response may occur instead of or as well as a physiologic response from stimulating a target nerve. In either case, a response from an important non-target nerve may indicate that it is unsafe to ablate as positioned. For example, an increase of central venous pressure (CVP) or pulmonary artery pressure (PAP) can indicate the desired response in combination with the reduction of Heart Rate (HR); however, a concomitant increase in HR may indicate that an important non-target nerve is within the stimulation zone and associated ablation zone (e.g. nerve stimulating an adrenal gland) and the ablation element and the associated stimulation element may be repositioned and confirmation of safety and efficacy may be reapplied. If both a target nerve and important non-target nerve are stimulated by the same stimulation signal then the nerves may be quite close together and delivering ablation energy may be unsafe. To avoid risk of injuring the non-target nerve the ablation element and stimulation element may be moved and stimulation repeated until a position is found that is both safe and effective. For example, the catheter can be advanced or different electrodes selected on the catheter placed along the azygos, hemiazygos or intercostal vein traveling along, crossing or traversing GSN and sympathetic chain (See FIG. 13). Alternatively, a catheter may comprise multiple ablation elements and corresponding stimulation elements positioned along a length (e.g., about 1 to 5 cm) of a distal segment of the catheter and stimulation regimens may be delivered to select a position among the multiple positions that is optimal.

Alternatively, a stimulation signal profile may narrow the stimulation zone to identify an appropriate ablation setting that would ablate the target nerve and not the non-target nerve. In another embodiment a catheter may comprise a stimulation element (e.g., at least one electrode or an electrode pair or pairs) having a stimulation zone that spatially corresponds with an ablation zone, and additionally have at least a second stimulation element that is far enough away from the ablation element(s) that the second stimulation zone corresponds to a region that is beyond the ablation zone. In this embodiment a physiologic response elicited by the second stimulation element and not the stimulation element associated with the ablation element may indicate safe positioning. In an embodiment wherein the ablation element is a cryo-ablation element, a cryo-mapping technique may be applied to cool the area and temporarily impede nerve conduction without permanently destroying the nerves. For example, the cryo-mapping technique may comprise delivering cryogenic energy from the cryo-ablation element but with a duration or temperature that only temporarily impedes nerve conduction. A physiologic response of a target nerve or non-target nerve to temporarily impeded nerve conduction may be different than a stimulated nerve. A temporarily impeded target nerve may have a similar response as an ablated target nerve but with a short duration.

Figure 13:
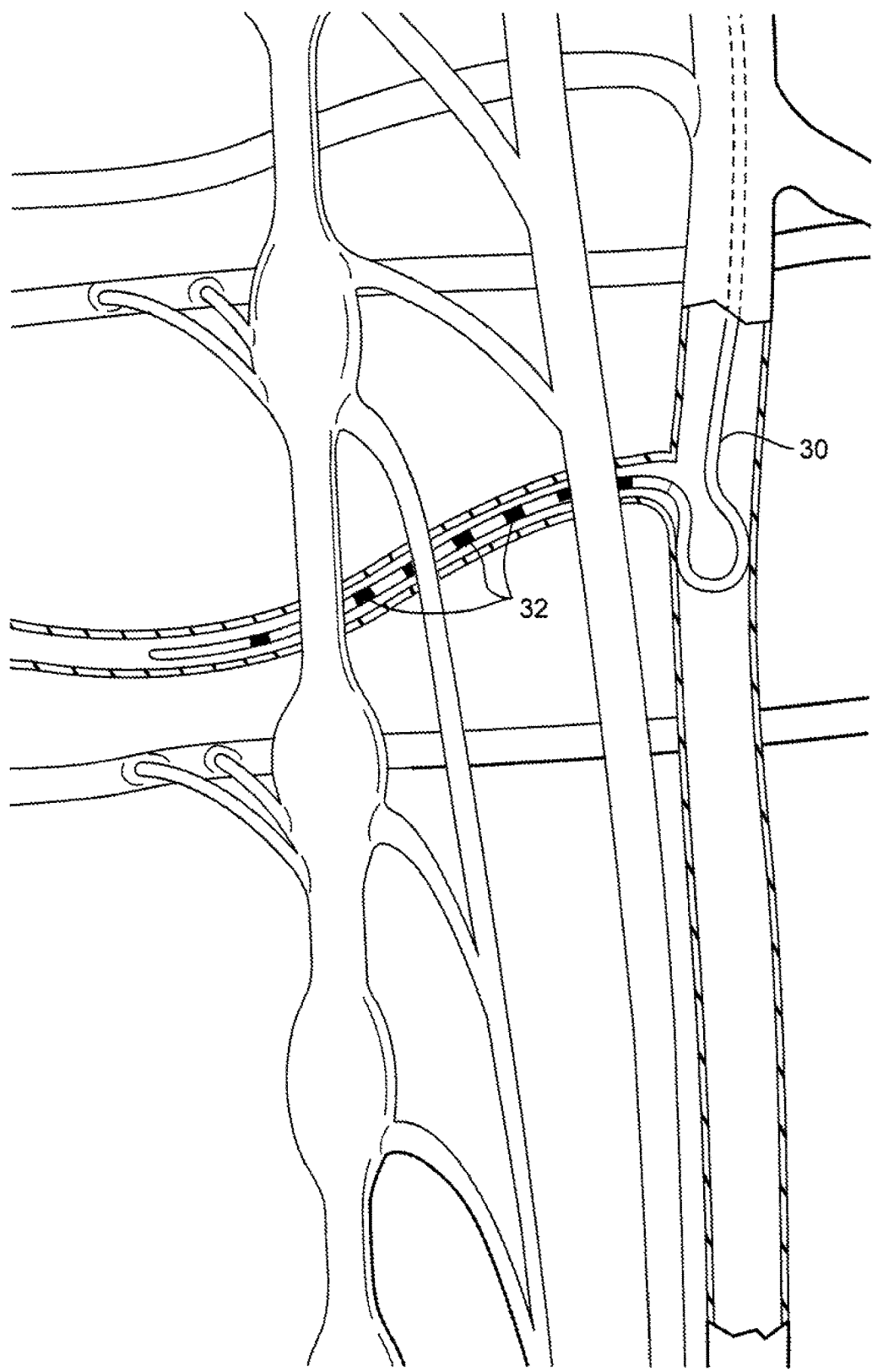
FIG. 13 shows a catheter suitable for stimulation and ablation deployed in an intercostal vein in close proximity to the GSN and sympathetic chain.

FIG. 13 is an illustration of an endovascular catheter 30 including multiple ablation and stimulation elements 32. The catheter is positioned in an intercostal vein via an azygous vein. The ablation and stimulation elements 32 may be on the surface of the catheter and positioned at regular increments along the length of a distal end region of the catheter.

The distal segment of the catheter can be navigated into the azygos and intercostal vein space of thoracic vertebrae T9, T10 or T11 as illustrated by FIG. 10. The catheter is in close proximity to both the GSN and the sympathetic chain. The diameter of the catheter where electrodes are located can be 2-6 mm and almost occluding and even possibly distending the intercostal vein. The targeted nerve can be identified by using electrical stimulation of the nerves along the catheter using selected electrodes as cathodes and anodes and monitoring the physiological responses.

Figure 14A:
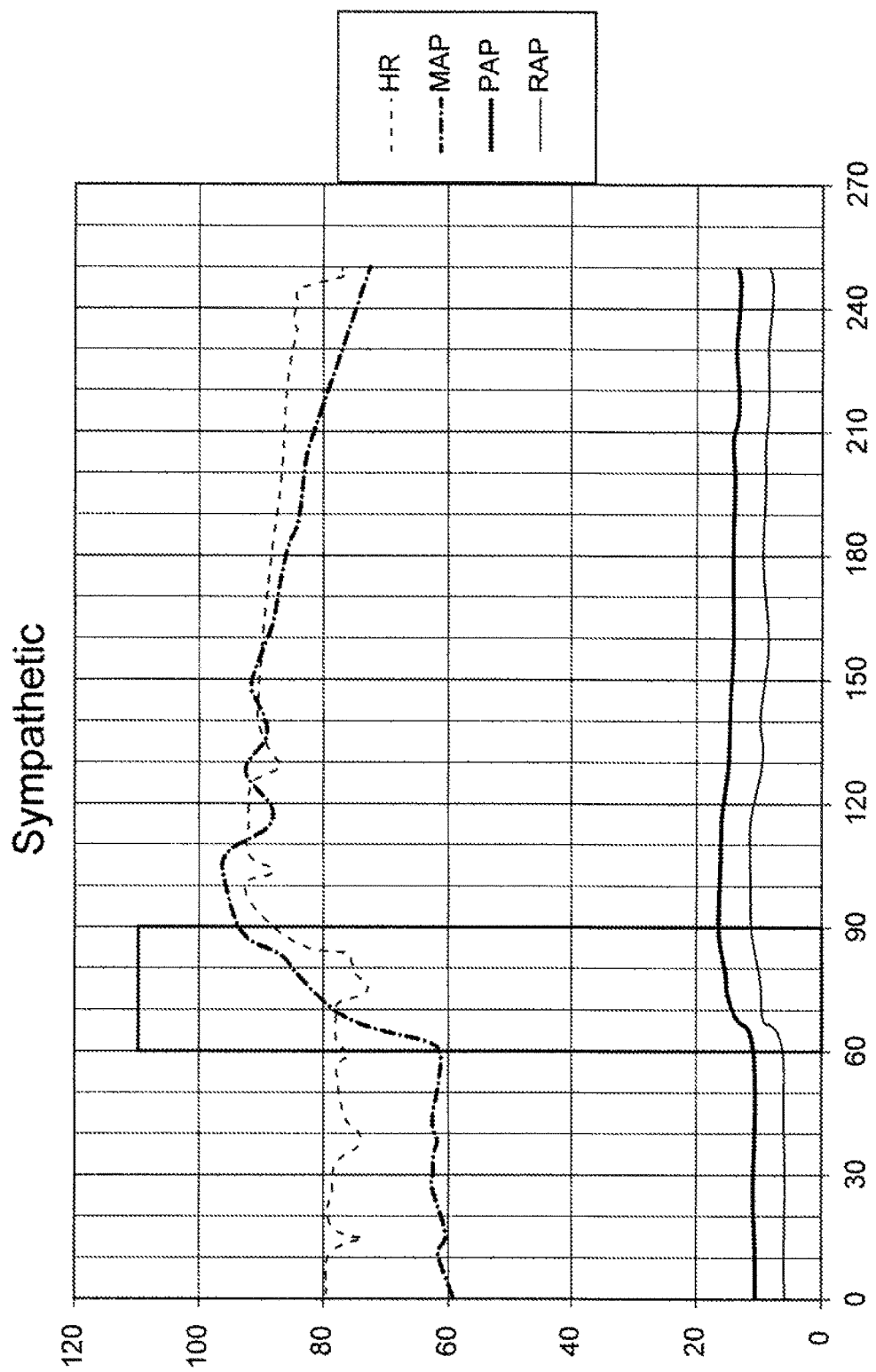
FIGS. 14A and 14B illustrate the different physiological responses between stimulation of the sympathetic chain (FIG. 14A) versus stimulation of the GSN (FIG. 14B).
Figure 14B:
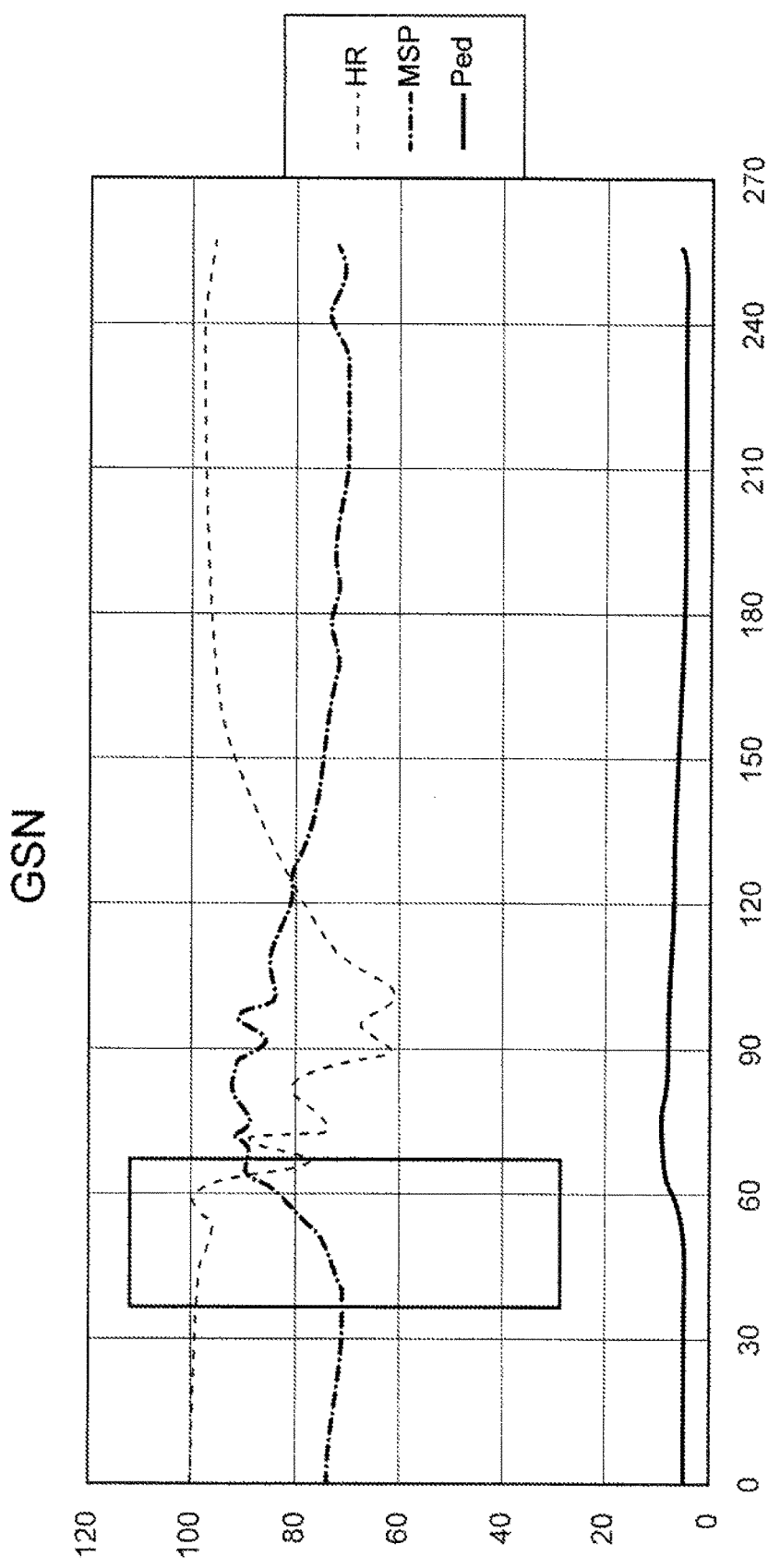

FIGS. 14A and 14B are plots of the different physiological responses observed during stimulation of the sympathetic chain and GSN in animals, respectively. In an animal study, the left sympathetic chain was stimulated via a catheter positioned in the intercostal vein at the T6 level. The HR and MAP increased during stimulation of the sympathetic chain as shown on FIG. 14A. The box illustrates time of application of energy between 60 and 90 seconds on X-axis. Changes in pulmonary artery pressure PAP and right atrial pressure RAP confirm that the preload of the heart increased in response to stimulation.

In a separate experiment the right GSN was selectively stimulated using a cuff electrode placed on the thoracic section of the GSN. Results are illustrated by FIG. 14B. During the GSN stimulation period shown as a box, mean systolic pressure (MSP) measured in the femoral artery increased while the HR decreased. The reduction of HR was likely caused by the normal compensatory response of the arterial baroreflex when the sudden upregulation of heart stroke volume is detected. Inventors confirmed that while blood flow in the inferior vena cava increased, cardiac output remained relatively constant. The Ped trace on FIG. 14B illustrates the increase of left ventricular end diastolic pressure (LVEDP) in response to the mobilization of fluid from the venous reserve.

To facilitate a clinically effective procedure, an embodiment may involve confirming that a patient will experience the desired physiologic effect of ablation before delivering ablation energy. This may be achieved by electrically, pharmacologically or cryogenically blocking the nerve temporarily and observing the physiologic response (e.g., hemodynamic effect). Optionally, vascular nerve mapping or confirmation of technically efficacious positioning as described herein to indicate that a target nerve is within an ablation zone or confirmation of safe positioning to indicate that an important non-target nerve is not within the ablation zone may first be done, then a temporary nerve block may be performed to assess potential clinical success. If potential clinical success is assessed to have a physiologic response as desired then ablation energy may be delivered to produce a permanent or more long lasting clinical effect, which may be analogous to the temporary clinical effect. Conversely, if the physiologic response to temporary blocking is not as desired, a physician may decide to not proceed with ablation. A different set of stimulation and ablation elements may be chosen to apply confirmation steps a different position may be found or the procedure may be aborted.

To facilitate a technically and clinically effective procedure, an embodiment may involve confirming that an ablation was successful and that the target nerve no longer conducts signals following delivery of ablation energy. This may be achieved by delivering stimulation signals with the same or different stimulation elements and observing the physiologic (e.g. hemodynamic) effect.

Since the greater splanchnic nerve tracks along the azygos vein for a considerable length, (e.g., up to about 3 to 5 cm), it may be possible to stimulate the greater splanchnic nerve distal to the ablation site and observe the absence of the hemodynamic effect. A device configured to stimulate distal to an ablation site may comprise a stimulation element having a stimulation zone associated with an ablation zone and additionally, a stimulation element positioned distal to the ablation element a sufficient distance to be beyond the ablation zone.

An embodiment of a method for confirming that the relative position of an ablation element to the target nerve (in this case a greater splanchnic nerve) is safe and technically effective before delivering ablation energy or selecting the appropriate ablation element and corresponding stimulation elements from a group of ablation and stimulation elements on a device may include the use of a mapping algorithm.

Figure 15:
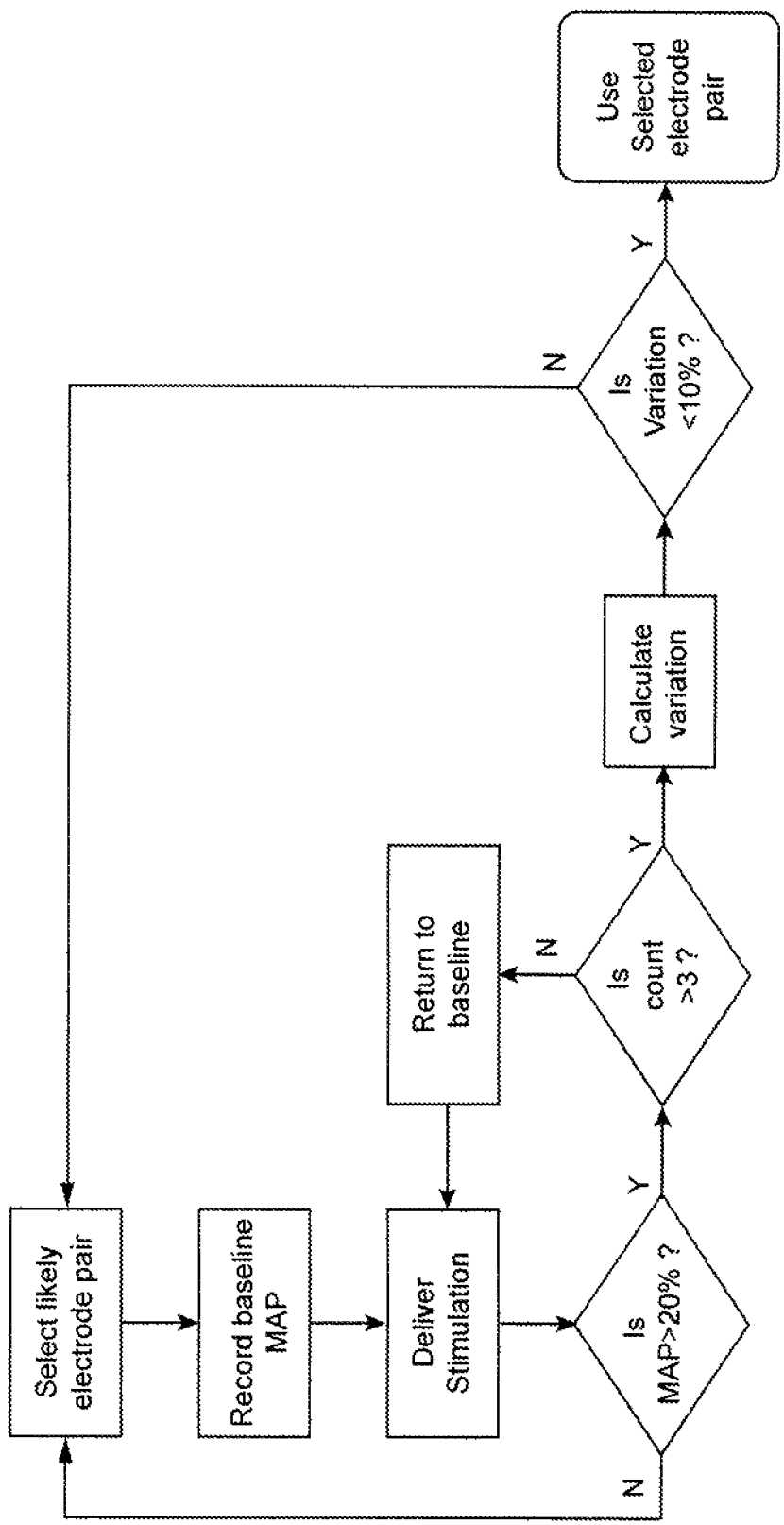
FIG. 15 is a mapping algorithm used to determine an optimal electrode pair that is based on in Mean Arterial Pressure (MAP) levels recorded after a stimulus is delivered.

The mapping algorithm, shown in FIG. 15 comprises the following steps:

(i) Select electrode pairs (ideally below T10 and above diaphragm or along the selected intercostal vein within 1-3 cm from azygos or hemiazygos branching). It is understood that electrode pairs refer to bipolar stimulation and ablation and one electrode may be selected if ablation or stimulation is monopolar.

(ii) Record a selected hemodynamic parameter (e.g. MAP, CVP, PAP, RAP) to establish the baseline. See, e.g., FIGS. 19A to 19D before "GSN cut".

(iii) Deliver Stimulation pulse with Current (I), pulse width (pw), frequency (F) and duty cycle (D) in about I=0-10 mA, pw=100-1000 us, F=20-40 Hz, D=50% for 20-60 s. On and at least 20-60 s OFF. (See FIG. 16).

(iv) Record a selected hemodynamic parameter or parameters (e.g. HR, MAP, CVP, PAP, RAP) such as shown in FIGS. 19A to 19D after GSN cut.

(iv) If the selected hemodynamic parameter >20% from baseline allow to return to baseline and possibly repeat.

Average measurements for 3 stimulations, for example, and if standard error is within +/−10%, the change in the selected hemodynamic parameter may be considered to be relevant.

Another method of confirming a suitable location for the ablation and stimulation elements prior to delivering ablation energy comprises a stimulation test in which a specific current, frequency and pulse width are selected (e.g., manually or automatically by a computerized algorithm) and stimulation is performed between pairs of electrodes that are in contact with the wall of the vessel (e.g., vein, azygos vein, hemiazygos vein). When the electric field is sufficient to activate the GSN, a rapid rise in Mean Arterial Pressure (MAP) or CVP or PAP and other hemodynamic changes occurs within a few seconds and can be graphically recorded and compared to assess ablation element placement.

A method of confirming technical success following delivery of ablation energy, in other words confirming that a target nerve has successfully been ablated may comprise the same or similar electrical stimulation parameters delivered from the same stimulation electrodes following ablation. Alternatively or additionally electrical stimulation may be delivered from stimulation electrodes positioned proximal to the location of an ablation (closer to the brain or sympathetic chain) where a physiologic response was elicited prior to ablating. Absence of responses or significant attenuation of responses will indicate technical success of the ablation.

Figure 16:
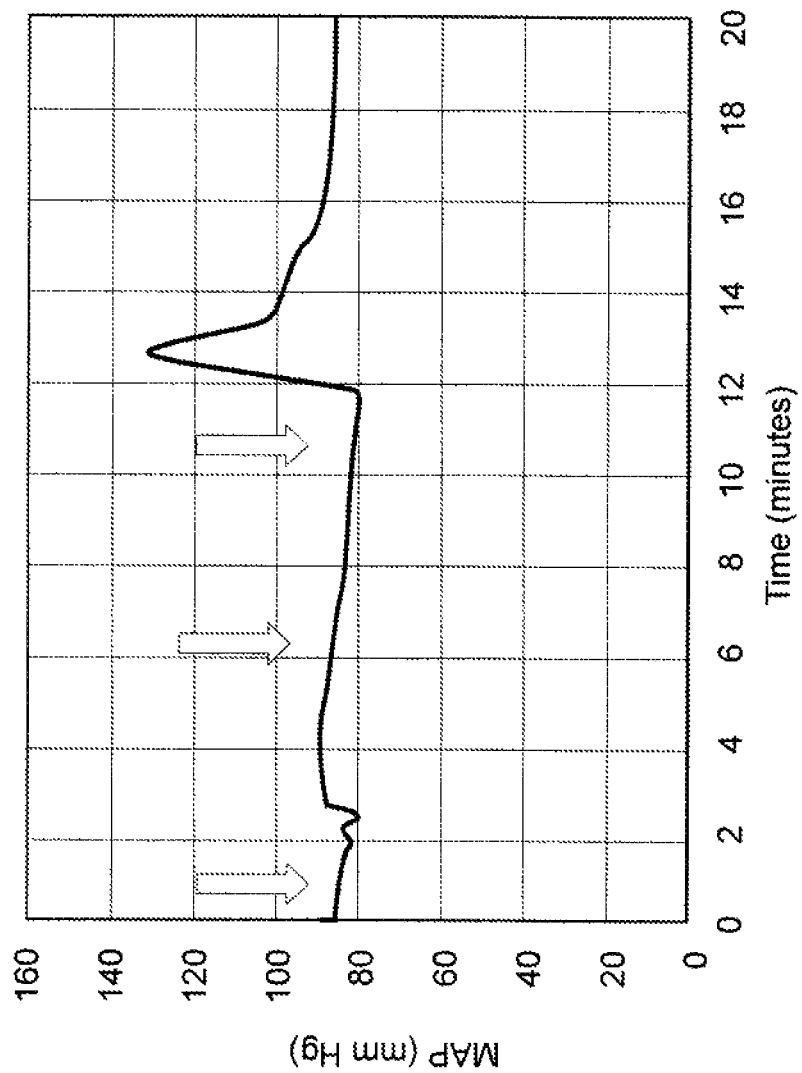
FIG. 16 is a plot of mean arterial pressure over time showing response to stimulation of an ablated nerve.

To confirm this notion FIG. 16 illustrates an experiment where the hemodynamic response to a greater splanchnic nerve stimulation and block with locally injected lidocaine, a nerve blocking agent, was tested in an animal. Time on the X-axis is in minutes. The Y-axis represents arterial blood pressure in mmHg. The first arrow from the left indicates the time of injection of lidocaine. The second arrow indicates the time of application of electrical stimulation to the greater splanchnic nerve proximal to the blocked area of the nerve. The term "proximal" as used herein with reference to a relative position on a nerve denotes a location nearer to a point of origin, such as brain, spinal cord, sympathetic chain or a midline of the body and where the term "distal" is used to denote a location further away from the point of origin and closer to the innervated peripheral organ such as splanchnic vascular beds, liver and spleen. Following the first stimulation proximal to the nerve block, no or very little physiologic response is observed on arterial blood pressure, or other physiologic parameters that are omitted on this graph for simplicity. The third arrow illustrates electrical stimulation of the greater splanchnic nerve for 30 seconds applied distal to the lidocaine blocked area. The physiologic response manifests by increase of mean arterial blood pressure and other hemodynamic parameters as described in this application. This experiment, performed using surgery, can be replicated using endovascular ablation with the use of appropriate tools and advanced imaging. Moving the stimulation electrode along the azygos vein, for example, to points distal and proximal the ablation lesion can confirm the effectiveness of ablation.

Alternatively switching between electrodes spaced along the length of the catheter (See FIG. 13 for example) can be used. A simple automation device can be envisioned to test different electrode pairs and measure responses then creating a report on the user interface.

Fluoroscopic imaging using body landmarks such as vertebrae, heart, veins and the diaphragm can be used to facilitate positioning of an ablation element or stimulation elements of a catheter. If the nerve were unsuccessfully ablated, which may be indicated by a positive hemodynamic change in response to stimulation of the greater splanchnic nerve proximal the ablation, then recourse may comprise ablation repeated at a higher energy level, ablation repeated at a different location, or improved electrode apposition.

It is noted that MAP monitoring as mentioned above is an example and hemodynamic monitoring does not necessarily need to be invasive monitoring and may be accomplished with a less invasive monitoring of blood pressure, for example using a Nexfin or ClearSight device (Edwards) for continuous monitoring of hemodynamics commonly used in hospitals. The ClearSight system quickly connects to the patient by wrapping an inflatable cuff around the finger. The ClearSight system provides noninvasive access to automatic, up-to-the-minute hemodynamic information including: SV, CO, SVR, or Continuous Blood Pressure (cBP). Such a monitoring device may be hooked up to a computerized console to communicate physiologic response to the computer, which may determine stimulation or ablation parameters based on the physiologic responses.

An embodiment of a system of the present invention may comprise an ablation catheter having at least one ablation element (e.g., RF electrode) and at least one associated stimulation element (e.g., stimulation electrode), a computerized console configured to generate and control delivery of a stimulation signal to the stimulation element, and a computerized console configured to generate and control delivery of an ablation signal (e.g., RF electrical current) to the ablation element. The stimulation console and the ablation console may be separate machines or integrated into one machine and may communicate to one another. The system may further comprise components necessary to support the type of ablation energy for example, if the ablation energy is RF electrical current the system may further comprise a dispersive grounding pad; if the ablation energy is a chemical agent the system may further comprise a means to inject the agent such as a manually operated syringe or automatically controlled pump. The system may further comprise a hemodynamic monitoring device that is in communication with the stimulation console or ablation console to provide feedback of hemodynamic response to stimulation or ablation. The computerized consoles may comprise algorithms that facilitate analysis of stimulation and hemodynamic response. For example, an algorithm may compute if a hemodynamic response to a stimulation is significant based on time of response, repeatability, difference from baseline.

Figure 18:
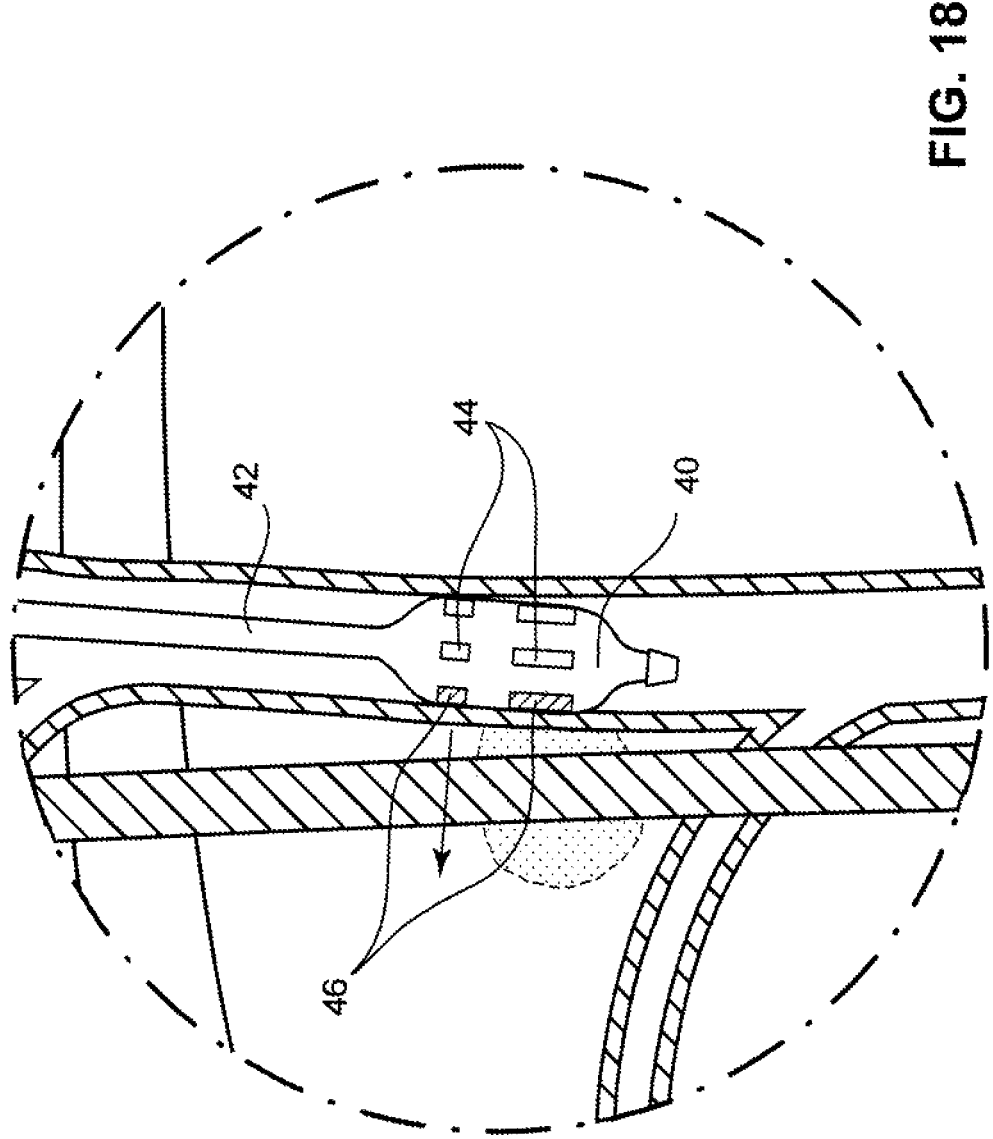
FIG. 18 is a schematic illustration of a distal end of an ablation catheter.
Figure 19C:
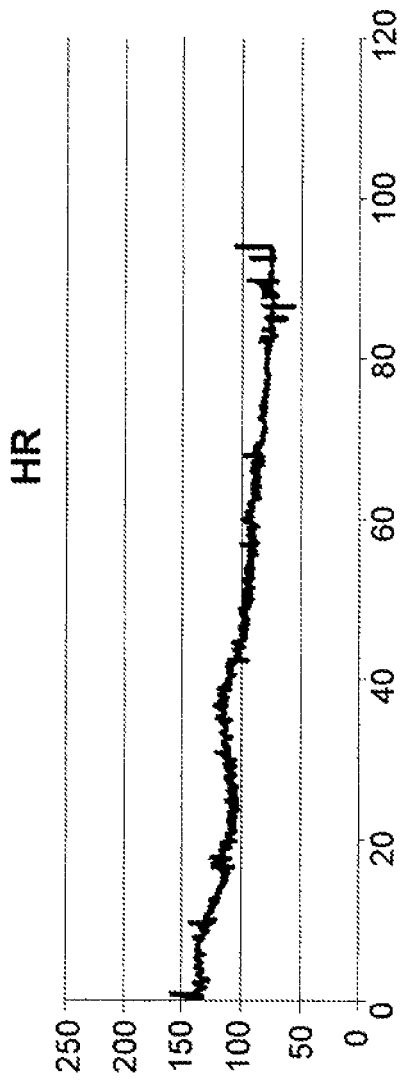
Figure 19D:
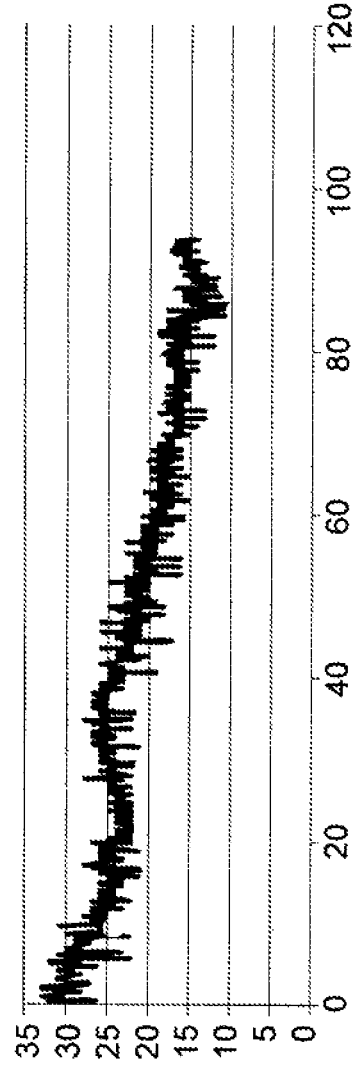

In embodiments wherein an ablation catheter comprises multiple ablation elements and associated stimulation elements, see FIGS. 13 and 18, an algorithm may facilitate selection of an optimal ablation element for example, based on strongest or quickest response to stimulation, and then deliver ablation energy to the selected ablation element. A console may comprise a graphical user interface that provides intuitive graphics or messages that help a user understand analysis of stimulation response.

Figure 17:
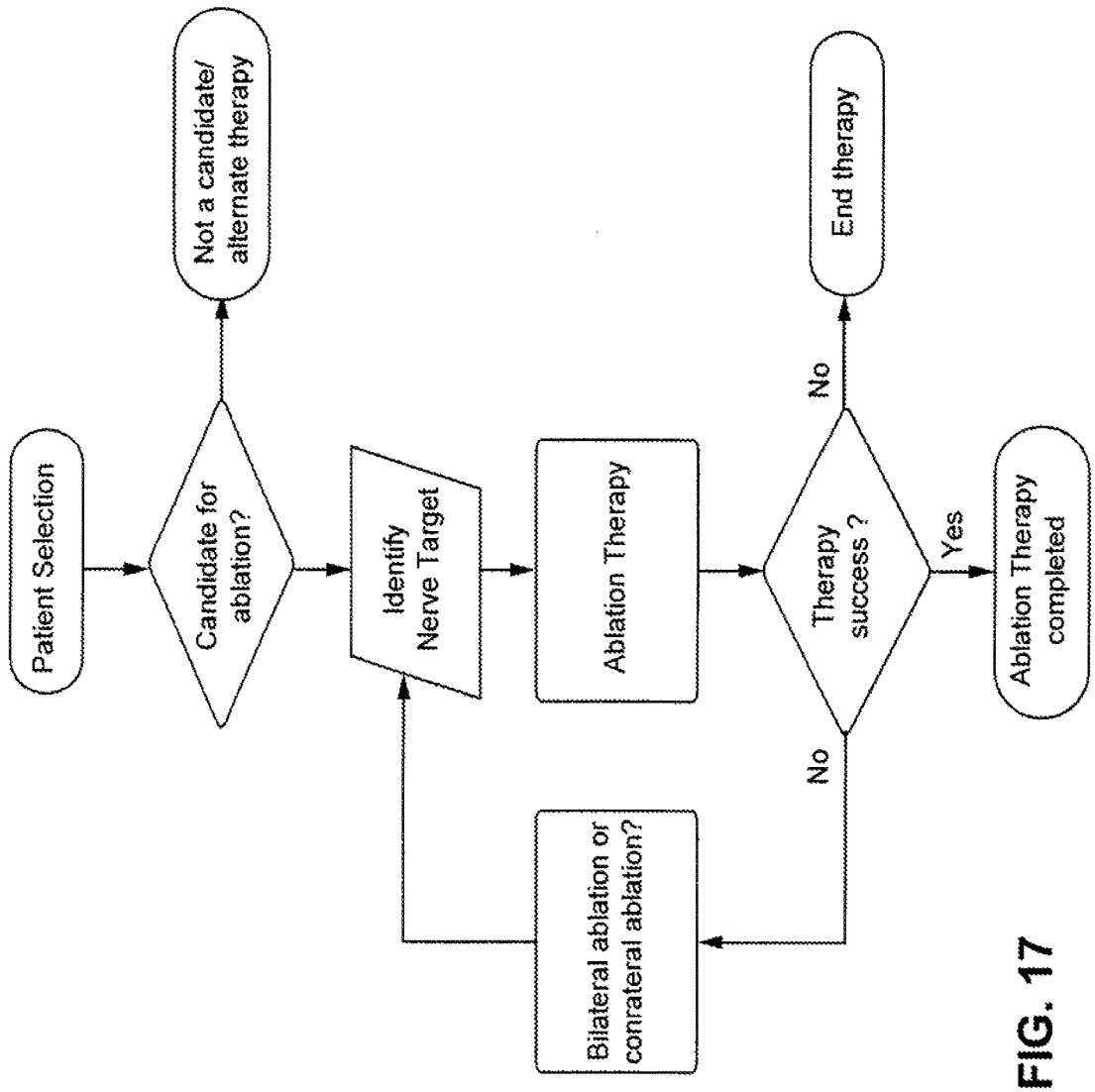
FIG. 17 is a flowchart illustrating the steps from patient selection to ablation therapy.

FIG. 17 is a chart that illustrates an example of patient flow from patient selection to the execution of ablation of the GSN to treat heart failure. One means for the selection of patients suitable for GSN ablation may include evaluation of splanchnic vascular capacitance. An orthostatic stress test (tilt table test), fluid challenge, exercise test or an appropriate drug challenge can help distinguish low vascular compliance from normal. Orthostatic stress causes blood shifts from the stressed volume to the unstressed volume. In healthy patients, to compensate for the shift, sympathetic tone increases resulting in splanchnic vasoconstriction and rapid mobilization of blood from the unstressed compartment to the active circulation. The hemodynamic response to tilt in chronic CHF is atypical, as there is not significant peripheral pooling in the upright posture indicating diminished splanchnic vascular capacitance. Acute oral or intravenous fluid challenge is another test to assess splanchnic vascular capacitance. A fluid challenge could test the capacitance by measuring the effects of a fluid bolus on cardiac filling and pulmonary pressures. Patients with low capacitance of the splanchnic venous reservoir will be unable to compensate for the hemodynamic effect of the fluid bolus. Patients with HF, HFPEF and patients with increased SNA will be more likely to respond to the fluid challenge with a disproportional rise in cardiac filing pressure and other related and measurable physiologic parameters. This response would indicate that the patient might be a candidate for GSN ablation therapy. After patient identification as a candidate for ablation therapy, the process of identifying the appropriate nerve target is implemented as the first step in the ablation procedure. Proper identification of the target nerve as well as non-target nerves or structures within the range of the ablative energy (mapping) is important to confirm the safety and efficacy of the ablation procedure.

FIGS. 13 and 14 illustrate a means for using differences in physiological responses to electrical stimulation to identify target nerve (GSN) and a nearby non-target or different target nerve (sympathetic chain). The choices of therapy can be made selectively by the physician based on the mapping information and the patient's individual responses and needs. For example an HFpEF patient with high chronic HR or BP (hypertension) may require different targeting than one with low blood pressure. After nerve target identification and selection, one optional means of confirmation of procedural efficacy is to temporarily block the nerve target and evaluate whether the physiological response is consistent with the desired clinical effect. After nerve target identification has been confirmed, the non-target nerves or other structures have been deemed outside of the range of ablation energy, and procedural efficacy has been confirmed; ablation therapy may be initiated.

Confirmation of the technical efficacy or success of the ablation procedure may be accomplished by delivering electrical stimulation proximal to the location of an ablation where a physiological response was elicited prior to ablation. Absence or attenuation of responses will indicate technical success of the ablation procedure (see FIG. 16). Another means of confirming technical efficacy may be evaluating splanchnic vascular capacitance (tilt table and/or fluid challenge) and compare to results before the procedure. If the ablation procedure is a success, no further action is needed. If the procedure is not successful, the clinician may opt to provide additional ablation therapy at the same site and/or repeat the procedure of identifying additional nerve targets (e.g, bilateral ablation) and providing ablation therapy as described previously.

Ablation Catheter Embodiment

FIG. 18 schematically illustrates a distal end of a catheter comprising a deployable balloon equipped with multiple surface electrodes capable of transvenous stimulation and RF ablation of a nerve from within a blood vessel. This device can be used in conjunction with hemodynamic monitoring to locate the greater splanchnic nerve, confirm a suitably safe and effective placement of ablation electrodes, ablate the greater splanchnic nerve, and confirm technical success of the ablation prior to withdrawing the device from the body and closing the venous puncture. In this embodiment the catheter shaft connects to a deployable structure such as a balloon, which is shown placed in an azygos vein and possibly distending the walls of the vein to bring ablation electrodes and stimulation electrodes in apposition with the walls of the vein. Application of a stimulation level current (energy) systematically from stimulation electrodes positioned around the balloon and in contact with the vein wall around its inner circumference while observing physiologic response may be done to identify where the greater splanchnic nerve is located along the circumference of the vein. If the electric field generated by the stimulation current from the electrode elicits the expected hemodynamic response, the longitudinally corresponding ablation electrode can be used to apply an ablation level of energy to create a lesion.

Application of stimulation current to the electrode following delivery of ablation energy while observing physiologic response can be used to confirm technical success, wherein absence or decrease of a physiologic response compared to the response observed prior to ablation may indicate that the nerve was successfully ablated.

In one embodiment, the catheter may be delivered transvenously through the cardiovascular system, specifically to the azygos vein via femoral access or internal jugular vein (IJV) access. It is envisioned that the ablation element may be positioned with or without the aid of a guide wire. When desired, a hollow, multi-pole catheter can be used to maintain natural flow levels within a blood vessel.

Stimulation elements used for confirmation of ablation element's position or confirmation of technical or clinical success are envisioned to contain one, two or more electrodes arranged in series or arrays, distributed and spaced circumferentially or longitudinally, which are chosen selectively to provide a sufficient, optimal, or a situational amount of electrical signaling. In these embodiments, the stimulation element may also have a plurality of electrodes that may be used initially to map a suitable location in an azygos or other suitable vein where the greater splanchnic nerve runs within close proximity for the length of 1-5 cm at a distance of about 1-5 millimeters, or crosses the vein, sometimes about 2-3 millimeters from the vein wall, through detecting a specific hemodynamic response to stimulation.

By way of example, the catheter and console system may comprise a catheter 10 having multiple electrodes spaced along a flexible shaft having a distal end region configured to be placed in an intercostal vein of a patient. The console is configured to generate and control delivery of ablation signals (high energy electrical pulses) and electrical stimulation signals (low energy electrical pulses). The low energy signals may include frequencies in the range of 5-50 Hz and high energy signals include frequencies in the range of 400-500 Hz. The low energy signal is selected to stimulate nerves proximate to the active electrode and the high energy signal is configured to ablate the nerves proximate to the active electrode. The signals are applied to the electrodes on the distal end region of the catheter. The console is capable of selectively applying low and high levels of energy to each the electrodes, such as by sequentially applying low energy pulses to all of the electrodes and applying high energy pulses to selected ones of the electrodes.

The console may be configured with a controller configured, e.g., programmed, to select and thereby activate an electrode and or group of electrodes (monopolar and/or bipolar) and; to select delivery of high or low energy. The selection means for selecting electrode and delivery can include a switch or program logic. The console may include physiologic monitoring device or devices in communication with the console, where the physiological monitoring device may include sensors located on the catheter device, elsewhere within the patient vasculature, and/or non-invasively.

A computer controller in the console may execute software and logic that include algorithms that facilitate analysis of hemodynamic and physiologic values recorded from patient monitoring device or devices in communication with the console. Examples of hemodynamic and physiological parameters are pupil dilation, increased sweating, increased heart rate, increased blood pressure, increased mean arterial pressure and any combination thereof.

The algorithms may confirm the positioning of the electrodes along the catheter in the intercostal vein with respect to the target nerve by automatically detecting a change in at least one selected hemodynamic or physiological parameter which occurs in response to the activation of an electrode on the catheter by a stimulation pulse. The algorithm may initially cause the recordation of a baseline vale of the hemodynamic parameter. Thereafter, algorithm causes stimulation pulse to be applied to the intercostal vein by one or more of the electrodes on the catheter. The stimulation pulse may have a current (I), a pulse width (pw), a frequency (F) and a duty cycle (D) wherein I=0-10 mA, pw=100-1000 us, F=20-40 Hz, and D=50% pulsing between 20-60 s. As each stimulation pulse is applied, the algorithm records the value of the selected hemodynamic or physiological parameter. The application of a stimulation pulse and recording the parameter value resulting from the pulse may proceed in a sequence for each of the electrodes on the catheter.

The recorded parameter values are used to select the electrodes are to receive an ablation pulse. The selection may be the electrode(s) corresponding to the largest change in the parameter value from the baseline value. Further, the selection may be to identify electrodes which, which applying the stimulation pulse, caused the parameter value to exceed a certain threshold, such as a twenty percent change (20%) from the baseline value.

To ensure a reliable parameter value, the stimulation pulse may be applied several times, such as three by each of the electrodes. The parameter value is recorded during each stimulation pulse. The average of the parameter values for each of the stimulation pulse applied to a specific electrode may be used as the parameter value to select an electrode for the ablation pulse. Also, a check may be made to the parameter values to conform that are within a certain range, such as within ten percent of each other. If any of the values are outside of the range, additional stimulation pulses may be applied to determine the average value or an alert may be generated by the console that is given to the health care provider.

The algorithm followed by the computer controller may be used to confirm a patient will experience the desired physiological effect of ablation before delivering ablation therapy is performed by an automated algorithmic process. Such an algorithm may include: temporarily blocking the target nerve with a stimulation signal, recording the physiologic response while the nerve is blocked, and evaluating the physiologic response to determine if the patient should undergo ablation of nerve by ablating the intercostal vein near the nerve. Clinical effectiveness is determined by comparing the recorded response to the desired physiologic response. The desired response may be progressive reductions in pressures (e.g., MAP, PAP, and LVEDP). The target nerve may also be temporarily blocked pharmacologically or cryogenically. If temporary blocking does not achieve the desired effect, the physician may decide not to proceed with ablation, select a different electrode configuration on the catheter to apply a stimulation signal and thereafter an ablation signal, or move rotationally or laterally the catheter and its electrodes in the intercostal vein.

The algorithm executed by the computer controller may also confirm the technical efficacy or success of the ablation procedure. The confirmation steps would be after (post) the ablation of the nerve via the intercostal vein. The conformation steps may include electrical stimulation by the catheter to a region of the intercostal vein the same as or proximal to the location of the ablation. The patient's response (physiological or hemodynamic) to the electrical stimulation is recorded and compared to the response prior to ablation. If the comparison indicates an attenuation or absence of a response, the algorithm will indicate technical success of the ablation procedure.

If the comparison indicates an unsuccessful ablation procedure, the physician or other health care provider may repeat the ablation therapy at the same site and/or repeat the therapy procedure for other nerve targets. Additional nerve targets could include bilateral ablation.

The console may include a graphical user interface configured to present information from the physiological signals where the information is the physiological response following (e.g., 5-60 seconds) the delivery of low and/or high energy and; algorithms that compare the physiologic signals to data from memory stored baseline values providing automated selection of appropriate electrode configurations and/or the appropriate energy delivery.

While certain forms of electrodes, or arrays/series of electrodes have been illustrated and described herein, it is not to be limited to the specific forms or arrangement of parts described and shown.

Studies:

It is known that clinically beneficial effects can be obtained in patients with heart failure by administering pharmacological therapies, such as nitroglycerine, to cause venodilation. These effects are immediate and pronounced in magnitude to the point where they can lead to severe side effects of low systemic blood pressure and poor vital organ perfusion. Stimulation of the GSN results in a rapid and large increase in blood pressure through a reduction in splanchnic vascular compliance, for example as shown by the experiment illustrated by FIG. 14. Thus, it was reasonable to be concerned that reduction in GSN activity by resection or ablation of the GSN could lead to the opposite effect, specifically to venodilation of the splanchnic circulation, resulting in a large, abrupt reduction in blood pressure and cardiac preload similar to that observed with pharmacological therapy.

An animal experiment was conducted to examine the worst case scenario, or total reduction in GSN activity, by cutting the GSN. A sharp, immediate reduction in blood pressure was anticipated. However, unexpectedly and counterintuitively, cutting of the GSN instead resulted in a slow, progressive reduction in pressures with unexpected beneficial changes in other hemodynamic measures.

Vascular capacitance can be increased in dogs with rapid pacing-induced heart failure by surgical resection or equivalent but less invasive percutaneous (through the chest wall) or transvenous ablation of a left or right greater splanchnic nerve resulting in profound improvement of cardiac function, pulmonary artery blood pressure and other relevant hemodynamic parameters. For the CHF patients such magnitude of changes can affect a number of clinical outcomes including mortality, exercise capacity, need for hospitalization and quality of life. While there may also be a place for controlled or intermittent inhibition of GSN activity in some patients, complete reduction in GSN activity may cause physiological changes that can result in clinically significant benefits in patients with heart failure and/or other diseases associated with fluid overload without the immediate side effects frequently seen with pharmacological therapy. Ablation of a nerve caused by an ablation catheter is envisioned to impede or eliminate signal transfer through a nerve similar to that caused by surgical resection.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention is:

1. A method for increasing splanchnic venous capacitance in a patient, comprising:
   positioning an endovascular catheter comprising a proximal region, a flexible shaft, and a distal region, wherein the flexible shaft connects the proximal and distal regions and is a length sufficient to access a T9, T10, or T11 intercostal vein of the patient relative to an access location when the proximal region remains external to the patient, and wherein the distal region is configured to be advanced through patient vasculature and dimensioned to terminate in the T9, T10 or T11 intercostal vein and make contact with an inner wall of the T9, T10 or T11 intercostal vein and comprises at least one ablation element, at least one stimulation element, and at least one detection element;
   advancing the distal region through an azygous vein;
   advancing the distal region from the azygous vein and into the T9, T10, or T11 intercostal vein;
   activating the at least one ablation element;
   ablating a greater splanchnic nerve using energy generated with the at least one ablation element; and
   removing the endovascular catheter from the patient.

2. The method of claim 1, further comprising confirming positioning success.

3. The method of claim 1, further comprising confirmation of an ablation of the greater splanchnic nerve.

4. The method of claim 1, wherein the proximal region comprises an energy source and a controller with embedded logic and software.

5. The method of claim 4, wherein the proximal region further comprises a user interface.

6. The method of claim 1, wherein the at least one ablation element is associated with the at least one stimulation element.

7. The method of claim 1, wherein the at least one detection element comprises at least one of a systemic, pulmonary arterial and venous pressure transducer, a cardiac output detector, or a blood flow monitor.

8. The method of claim 1, further comprising positioning a second detection element in a different part of the patient vasculature than the T9, T10 or T11 intercostal vein.

9. The method of claim 1, wherein the at least one ablation element comprises at least one of an electrode, a cryo console, a drug delivery device, an injection of neurolytic blocking agent, an ultrasound device, a radio frequency device, a thermal ablation device, or a laser emitter.

10. The method of claim 9, wherein the at least one ablation element comprises a radio frequency device that outputs an electrical current having a frequency in a range of 350 to 500 kHz and a power in a range of 5 to 50 W.

11. The method of claim 1, wherein the at least one detection element comprises a blood pressure transducer.

12. The method of claim 1, wherein the at least one detection element comprises a tissue temperature sensor.

13. The method of claim 1, wherein the at least one detection element comprises a hemodynamic sensor.

14. The method of claim 1, wherein the at least one detection element comprises an environmental temperature sensor.

15. The method of claim 1, wherein the at least one detection element comprises a tissue impedance sensor.

16. The method of claim 1, wherein the distal region comprises a deployable structure comprising at least one of a balloon, a cage, a basket, a preformed shape, lasso or loop.

17. The method of claim 1, wherein the access location is a radial, brachial, subclavian, jugular or femoral vein.

18. The method of claim 1, wherein the positioning step is proceeded by an introduction and advancement of a guide-wire to facilitate advancement of the endovascular catheter through the patient vasculature.

19. The method of claim 1, wherein the at least one ablation element and the at least one stimulation element are positioned on the endovascular catheter relative to one another so that an area in which a stimulation signal delivered by the at least one stimulation element correlates with an ablation zone in which the energy delivered by the at least one ablation element is sufficient to cause irreversible ablation of the greater splanchnic nerve.

20. The method of claim 2, wherein confirming the positioning success of the distal region is performed by an automated algorithmic process to confirm a change in at least one selected hemodynamic or physiological parameter.

21. The method of claim 20, further comprising selecting an electrode or an electrode pair of the at least one stimulation element, recording a baseline of the selected hemodynamic parameter, delivering a stimulation pulse with a current (I), a pulse width (pw), a frequency (F) and a duty cycle (D) in about I=0-10 mA, pw=100-1000 us, F=20-40 Hz, D=50% pulsing between 20-60 s; and recording a measurement of the selected hemodynamic parameter.

22. The method of claim 21, further comprising determining if the measurement of the hemodynamic parameter is >20% from the baseline, allowing the selected hemodynamic parameter to return to the baseline and repeating for at least three measurements, recording average measurements for the at least three measurements, and if a standard error is within +/−10%, confirming the change in the at least one hemodynamic parameter or physiological parameter.

23. The method of claim 20, wherein the at least one selected hemodynamic or physiological parameter is selected from the group of responses consisting of pupil dilation, increased sweating, increased heart rate, increased blood pressure, and increased mean arterial pressure.

24. The method of claim 1, further comprising
applying electrical stimulation to the greater splanchnic nerve;
detecting physiological changes to confirm positioning success; and
re-applying electrical stimulation to the greater splanchnic nerve to confirm irreversible ablation of the greater splanchnic nerve.

25. The method of claim 24 further comprising re-positioning the distal region, and repeating the applying the electrical stimulation until positioning success is confirmed.

26. A method for increasing splanchnic venous capacitance in a patient, comprising:
positioning an endovascular catheter comprising a proximal region, a flexible shaft, and a distal region, wherein the flexible shaft connects the proximal and distal regions and is a length sufficient to access a T9, T10, or T11 intercostal vein of the patient relative to an access location when the proximal region remains external to the patient, the distal region comprising at least one ablation element;
advancing the distal region through an azygous vein;
advancing the distal region from the azygous vein and into the T9, T10, or T11 intercostal vein;
activating the at least one ablation element;
ablating a greater splanchnic nerve using energy generated with the at least one ablation element; and
removing the endovascular catheter from the patient.

27. The method of claim 26, further comprising confirming a proper position of the at least one ablation element in the T9, T10 or T11 intercostal vein.

28. The method of claim 26, further comprising confirming that the greater splanchnic nerve has been ablated.

29. The method of claim 26, wherein the at least one ablation element comprises a balloon, the method further comprising expanding the balloon in the T9, T10, or T11 intercostal vein prior to the ablating with the at least one ablation element.

30. The method of claim 29, wherein the balloon has a cylindrically shaped expanded configuration, wherein expanding the balloon comprises expanding the balloon towards the cylindrically shaped configuration.

31. The method of claim 29, wherein expanding the balloon comprises expanding the balloon to have a diameter from 2 mm-6 mm.

32. The method of claim 29, wherein expanding the balloon comprises distending a wall of the T9, T10, or T11 intercostal vein.

33. The method of claim 26, wherein advancing the distal region from the azygous vein and into the T9, T10, or T11 intercostal vein comprises advancing the distal region into a right T9, T10, or T11 intercostal vein.

* * * * *